(12) United States Patent
Mathew et al.

(10) Patent No.: US 7,074,935 B2
(45) Date of Patent: Jul. 11, 2006

(54) METHODS FOR THE SYNTHESES OF ALFENTANIL, SUFENTANIL AND REMIFENTANIL

(75) Inventors: Jacob Mathew, Fenton, MO (US); J. Kendall Killgore, St. Louis, MO (US)

(73) Assignee: Mallinckrodt Inc., St. Louis, MO (US)

( * ) Notice: Subject to any disclaimer, the term of this patent is extended or adjusted under 35 U.S.C. 154(b) by 389 days.

(21) Appl. No.: 10/130,324

(22) PCT Filed: Dec. 4, 2000
(Under 37 CFR 1.47)

(86) PCT No.: PCT/US00/32882

§ 371 (c)(1),
(2), (4) Date: May 14, 2002

(87) PCT Pub. No.: WO01/40184

PCT Pub. Date: Jun. 7, 2001

(65) Prior Publication Data

US 2004/0138461 A1    Jul. 15, 2004

Related U.S. Application Data

(60) Provisional application No. 60/168,739, filed on Dec. 6, 1999.

(51) Int. Cl.
*C07D 401/06* (2006.01)
(52) U.S. Cl. .................................... 546/210
(58) Field of Classification Search ................. 546/210
See application file for complete search history.

(56) References Cited

U.S. PATENT DOCUMENTS

| 3,161,644 A | 12/1964 | Janssen et al. |
| 3,998,834 A | 12/1976 | Janssen et al. |
| 4,167,574 A | 9/1979 | Janssens |
| 5,019,583 A | 5/1991 | Feldman et al. |
| 5,489,689 A | 2/1996 | Mathew |

FOREIGN PATENT DOCUMENTS

| GB | 1 598 872 | 9/1981 |
| WO | WO 95/09152 A1 | 4/1995 |
| WO | WO 95/09155 | 4/1995 |

OTHER PUBLICATIONS

Janssens, F. et al., "Synthesis 1, 4-Disubstituted-1,4-dihydro-5H-tetrazol-5-one Derivatives of Fentanyl: Alfentanil ® 39209), a Potent, Extremely Short-Acting Narcotic Analgesic", J. Med. Chem., (1986), pp. 2290-2297, vol. 29:11.

Meuldermans, W. et al., "Excretion and Biotransformation of Alfentanil and Sufentanil in Rats and Dogs", Drug Metabolism and Disposition, (1987), pp. 905-913, vol. 15:6.

*Primary Examiner*—Patricia L. Morris

(57) ABSTRACT

Synthetic pathways are disclosed for synthesizing derivatives or analogs of fentanyl. Specifically set out are pathways for synthesizing alfentanil, sufentanil and remifentanil. The disclosed methods require fewer steps and produce a greater yield of product than methods reported in the prior art. The pathways to all these compounds begin with a common pathway of condensing a piperidone with a primary amine so as to form a 4-amino carboxyamino-piperidine, wherein N of said piperidone is a —N—COO—$(CH_2)_n$$CH_3$, alkylating an N of said primary amine which was condensed with said piperidone thereby producing an N-alkyl-anilide, and hydrolyzing said —COO—$(CH_2)_n$$CH_3$? group of said 4-amino-4-carboxyamino-piperidine following the condensation reaction so as to form a piperidine hydrolysis product. This product can then be convened to remifentanil in a 4 step reaction. Also, this hydrolysis product can be treated with a hydride to yield a 4-hydroxymthyl-piperidine which can be converted to alfentanil in 3 further steps, to sufentanil in 3 more steps, or to a variety of remifentanil analogs in two steps.

1 Claim, No Drawings

METHODS FOR THE SYNTHESES OF ALFENTANIL, SUFENTANIL AND REMIFENTANIL

This application is a Provisional of 60/168,739 filed Dec. 6, 1999.

BACKGROUND OF THE INVENTION

Fentanyl is a synthetic opioid. As a result of fentanyl's clinical success and the need to more clearly define the structural requirements necessary for its µ opioid agonist efficacy, extensive efforts have been devoted to developing the structure activity relationships of the 4-anilidopiperidine class of analgetics (Borne et al., *J. Med. Chem.* 27:1271 (1984); Janssen, U.S. Pat. No. 3,161,644 (1964); Kudzma et al., *J. Med. Chem.* 32:2534 (1989); Colapret et al., *J. Med. Chem.* 32:968 (1989); Janssens et al., J. Med. Chem. 29:2290 (1986)). As a result of these efforts, two congeners of fentanyl, alfentanil and sufentanil, were discovered and have found clinical utility as anesthesia adjuncts. In comparison with fentanyl, alfentanil has a shorter duration of action and sufentanil has 5–10 fold greater potency.

With the emphasis in anesthetic and surgical practice focusing on shorter and outpatient surgical procedures, the need for an ultrashort acting opioid analgetic has surfaced. Although alfentanil is considered an ultrashort acting agent, its terminal half-life in humans, approximately 70–90 minutes, is longer than desired for certain procedures. The ideal ultrashort-acting analgetic should have a biological half life ranging from 1–30 minutes. In this case, rapid elimination or biotransformation of such an agent to inactive or less active products would minimize. accumulation and subsequent redistribution with prolonged or repeated administration. Furthermore, respiratory depression and muscle rigidity, two well documented µ opioid effects with agonists of high intrinsic efficacy, would be of short duration.

In order to discover an analgetic with the desired profile, the 4-anilidopiperidine structure was modified such that the metabolism could be achieved through a rapid enzymatic reaction in the blood (Feldman et al., *J. Med. Chem.* 34:2202 (1991)).

The two most commonly used piperidine nitrogen substituents in these analgetics are the phenethyl and 2-thienylethyl both of them being very lipophilic. The strategy of Feldman et al. involved replacing the aryl groups with a lipophilic group that would still retain the binding characteristics of the aryl groups, but upon enzymatic degradation would yield a polar group with less affinity for the µ receptor, and greater chances for rapid elimination (U.S. Pat. No. 5,019,583).

As a result of extensive testing of several of these analogs, Remifentanil has emerged as a potent opioid analgesic with an extremely short half-life (10–20 minutes) (Amin et al., *J. Pharmacol. Exp. Ther.* 274:34 (1995)) and has undergone successful clinical trials and is awaiting FDA approval.

The instant invention is an improved method of synthesizing 4-anilidopiperidine derivatives, especially alfentanil, sufentanil and remifentanil.

Alfentanil is a member of the series of potent fentanyl analogues. The chemical name for alfentanil is: propanamide, N-[1-[2-(4-ethyl-4,5-dihydro-5-oxo-1H-tetrazol-1-yl)ethyl]-4-(methoxymethyl)-4-piperidinyl]-N-phenyl-. It is also called: N-1{1-{2-(4-ethyl-4,5-dihydro-5-oxo-1H-tetrazol-1-yl)ethyl}-4-(methoxymethyl)-4-piperidinyl}-N-phenylpropanamide. It was first synthesized in 1976 (U.S. Pat. No. 4,167,574). Alfentanil appears to have most of the properties sought in the ideal analgesic. These are 1) reliable, dose-related analgesia, 2) rapid onset, 3) duration adaptable to clinical situation, 4) minimal cardiovascular impairment, and 5) fast, complete recovery, without hangover (Drugs of Today, volume 20(1) (1984)). The analgesic potency of alfentanil is one-quarter that of fentanyl. The duration of its action is one third that of an equianalgesic dose of fentanyl and is clearly dose-related. Its depressant effects on respiratory rate and alveolar ventilation are also of shorter duration than those of fentanyl, and in most cases the analgesic effect lasts longer than the respiratory depression. The onset of action of alfentanil is 4 times more rapid than that of an equianalgesic dose of fentanyl and the peak analgesic and respiratory depressant effects occur within 90 seconds of administration.

The acute intravenous (i.v.) toxicity of alfentanil was studied in rats and an $LD_{50}$ of 47.5 mg/kg was established whereas fentanyl's $LD_{50}$ was 3.05 mg/kg i.v.

In man, the mean elimination half-lives of alfentanil and fentanyl were found to be 1.63 and 3.09 hours, respectively (Bower and Hull, *Brit. J Anaesth.* 54:871–887 (1982)). Plasma protein binding of alfentanil was significantly greater than that for fentanyl, and alfentanil did not bind to erythrocytes. It is also less lipid soluble than fentanyl and has a much lower volume of distribution relative to fentanyl (0.86 vs. 4.21 per kilogram). Alfentanil appears to be unique among the opioids in having a small apparent volume of distribution and low clearance (Stanski and Hug, *Anesthesiol.* 57:435–438 (1982)).

The rapid onset and short duration of action makes alfentanil particularly suitable for surgical procedures of short duration, such as day case surgery or where a rapid suppression of reflex responses is required. Cardiovascular parameters remain stable and recovery is remarkably fast and complete (Sinclair and Cooper, *Anaesthesia* 38:435–437 (1983)).

Although alfentanil is considered a short-acting analgesic, especially suited for brief surgical procedures, the drug can also be used for longer operations. In this case, a bolus of alfentanil must be followed by an infusion at a rate sufficient to compensate for the disappearance of the drug due to redistribution and elimination (Noorduin et al., *Drug Dev. Res.* 8:347–352 (1986)). In view of its brief but controllable action, alfentanil may prove of particular value in patients undergoing acutely painful but transient procedures such as reduction of fractures, dilatation and curettage, as well as in painful dental conditions.

Sufentanil citrate, first synthesized in 1974 (Niemegeers et al., *Arzneim. Forsch.* 26:1551–1556 (1976)), is a piperidine derivative and a member of a series of potent fentanyl analogues. It is a powerful analgesic with an excellent safety margin as compared to other narcotic agents. It is furthermore characterized by a high selectivity and affinity (approximately 10 times greater than fentanyl) for "mu" opiate receptors. Sufentanil produces, unlike fentanyl or morphine, complete anesthesia with minimal side-effects. When compared with fentanyl, its pharmaco-kinetic profile in man shows a smaller volume of distribution, resulting in a terminal half-life intermediate between alfentanil and fentanyl. Sufentanil in high doses with 100% oxygen in patients undergoing major surgical procedures produces excellent cardiovascular stability and preserves cardiac output and myocardial oxygen balance with minimal changes in heart rate. Furthermore, sufentanil suppresses most hormonal responses to surgical stimulation without producing significant cardiovascular depression. Additionally, sufentanil, like fentanyl, does not cause histamine release. Also, in low to moderate doses, sufentanil may have further advantages over other narcotic agents. When compared with meperidine, morphine and fentanyl, in patients undergoing general surgery under balanced anesthesia, sufentanil provides stable cardiovascular parameters, low preoperative catecholamine plasma levels, very little need for additional inhalation supplementation, and a low incidence of postoperative respiratory depression.

Because of its remarkably low cardiovascular toxicity, sufentanil citrate has been evaluated as a total intravenous anesthetic for major surgical procedures. It is primarily used for open heart surgery and major operations in patients with severe cardiovascular compromise.

The chemical name for sufentanil is N-[4-(methoxymethyl)-1-[2-(2-thienyl)ethyl]-4-piperidinyl]-N-phenylpropanamide. In its citrate form the chemical name is N-[4-(methoxymethyl)-1-[2-(2-thienyl)ethyl]-4-piperidinyl]-N-phenylpropanamide, 2-hydroxy-1,2,3-propanetricarboxylate. The citrate form has an empirical formula of $C_{28}H_{38}N_2O_9S$. Sufentanil citrate is a white crystalline powder (molecular weight=578.68) with a reported melting point of 136.3° C., and is very soluble in water and most common organic solvents.

Synthesis of sufentanil is disclosed in U.S. Pat. No. 3,998,834 to Janssen. The process described therein, however, is quite lengthy and complicated. An improved synthesis is described in U.S. Pat. No. 5,489,689 to Mallinckrodt. The present invention is an improvement over the Janssen method and an alternative procedure to the procedure of the '689 patent.

While the 4-anilidopiperidine opioid analogues exemplified by fentanyl (1b) are readily

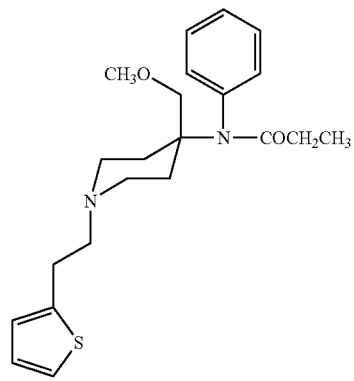

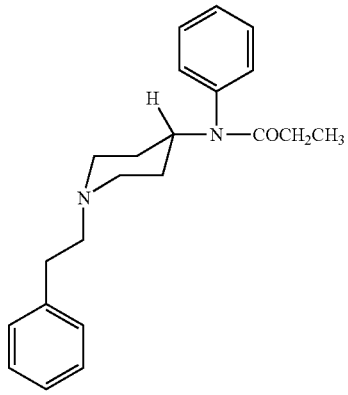

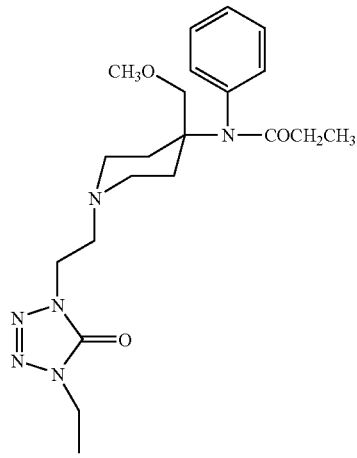

prepared, the 4-alkyl analogues such as Sufentanil (1a) and alfentanil (1c) have been more difficult. Alfentanil HCl is currently supplied by Janssen Pharmaceutical, Ltd. (Belgium). The Janssen syntheses of sufentanil and alfentanil proceed in 10 steps in low overall yield (~2%) (Scheme I). Modifications have improved the yield in the conversion of nitrile 2 to ester 5. The Janssen synthesis commences with the condensation of N-benzyl-4-piperidone with aniline in the presence of potassium cyanide (the Strecker synthesis) to yield the cyanoamine 2. Sequential hydrolysis of cyanoamine 2 to anilino amide 3 (concentrated sulfuric acid) and then to the corresponding acid 4 was achieved with concentrated hydrochloric acid at reflux. Esterification of the acid 4 gave ester 5 which on reduction with lithium aluminum hydride gave 4-(hydroxymethyl)4-anilino-N-benzylpiperidine 6. The alcohol 6 was etherified (NaH, MeI, HMPA) to give the methyl ether 7 and then propionylated to give the amide 8. The amide was subjected to hydrogenolysis of the N-benzyl protecting group and the resulting secondary amine 9 was N-alkylated with either the thiophene side chain or the tetrazole side chain to generate sufentanil (shown in Scheme I) or alfentanil.

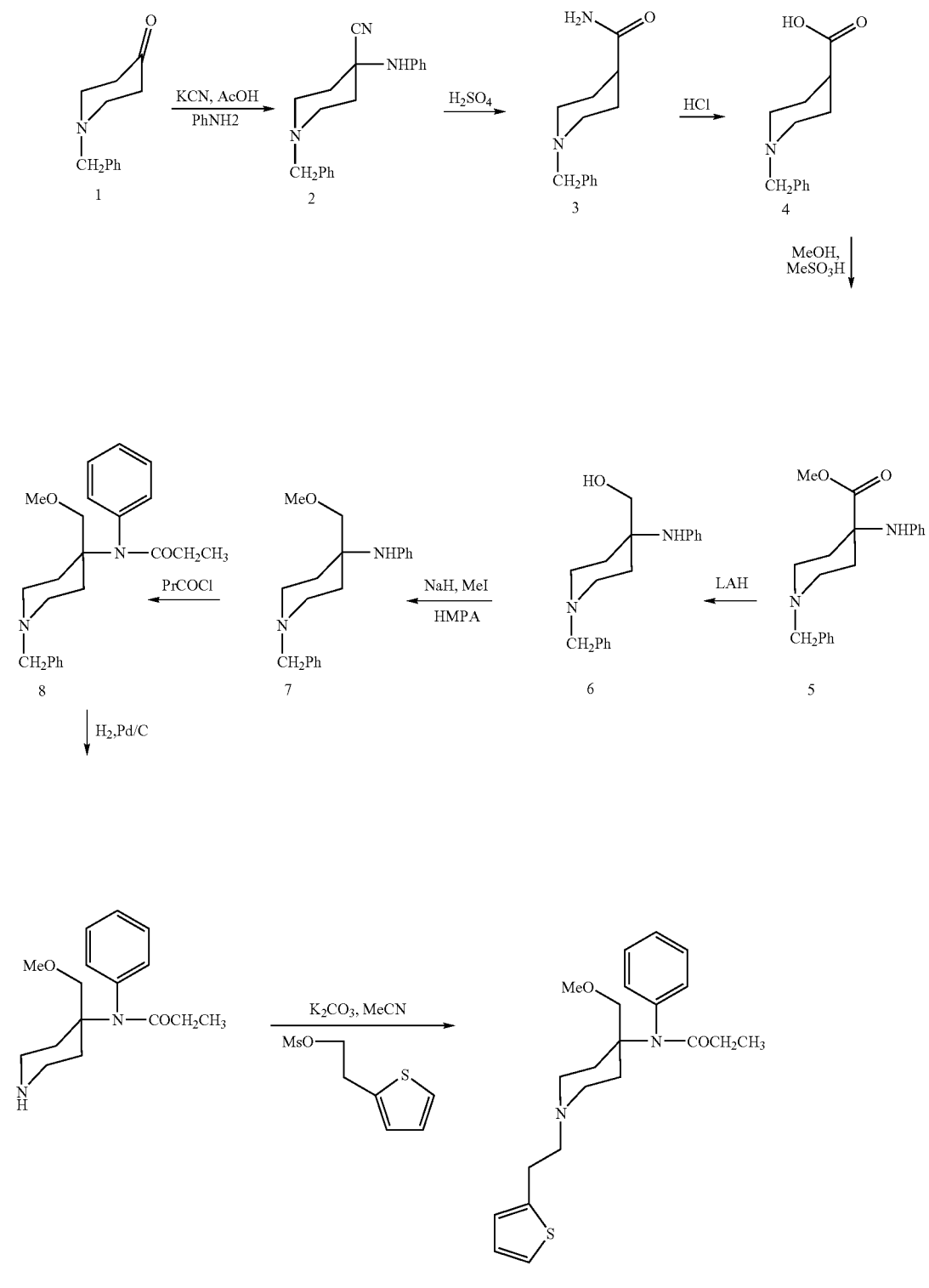

For large scale production, use of cyanide in the initial step is undesirable from a safety and environmental point of view. Another problem that complicates this scheme is the tendency of the secondary piperidines 9 to suffer an intramolecular acyl-group migration (Scheme II) upon standing (either neat or in solution) (Colapret et al., J. Med. Chem. 32:968 (1989)). The analogous O to N acyl migration has been well precedented.

SCHEME II

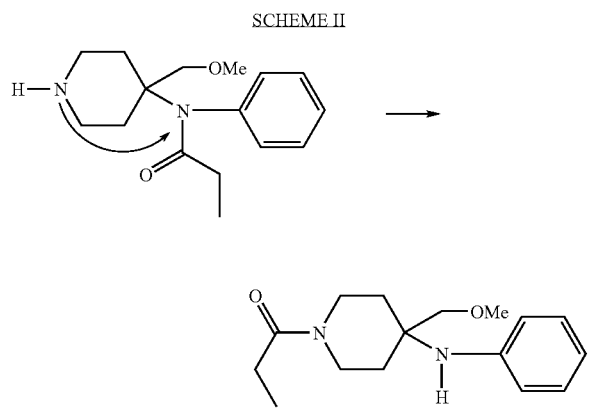

SUMMARY OF THE INVENTION

Methods for preparing alfentanil, sufentanil and remifentanil and derivatives are described herein which require fewer steps than the methods known in the prior art. The overall yield for alfentanil is also better than the method known in the prior art, the yield obtained with the presently disclosed method being approximately 16%. The resulting product is approximately 99% pure. Results for the synthesis of sufentanil are expected to be similar. The disclosed method for alfentanil is a 7 step synthetic process, with the final 6 steps shown in Scheme III. The process begins with N-carbethoxy-4-piperidone. This is converted to 1-(carbethoxy)-4-(phenylamino)-4-piperidinecarboxanilide. Step 2 is the formation of (1-carbethoxy)-4-(phenylamino)-4-piperidinecarbox(N-methyl)anilide. This is treated in step 3 with isopropanol and KOH to yield 4-(phenylamino)-4-piperidinecarbox-(N-methylanilide). Step 4 is a superhydride treatment to form 4-(phenylamino)-4-(hydroxymethyl)piperidine. This compound in turn is reacted with 1-(2-bromoethyl)-4-ethyl-1,4-dihydro-5H-tetrazol-5-one to form the step 5 product of N-{1-{2-(4-ethyl-4,5-dihydro-5-oxo-1H-tetrazol-1-yl)ethyl}-4-(phenylamino)-4-(hydroxymethyl)piperidine. In step 6, the step 5 product is treated with NaH, tetrahydrofuran, MeI and 15-Crown-5 to eventually produce N-{1-{2-(4-ethyl-4,5-dihydro-5-oxo-1H-tetrazol-1-yl)ethyl}-4-(phenylamino)-4-(methoxymethyl)piperidine}. The final step is to react this with propionyl chloride in chloroform to produce alfentanil. The 7 steps require the inclusion of

SCHEME III

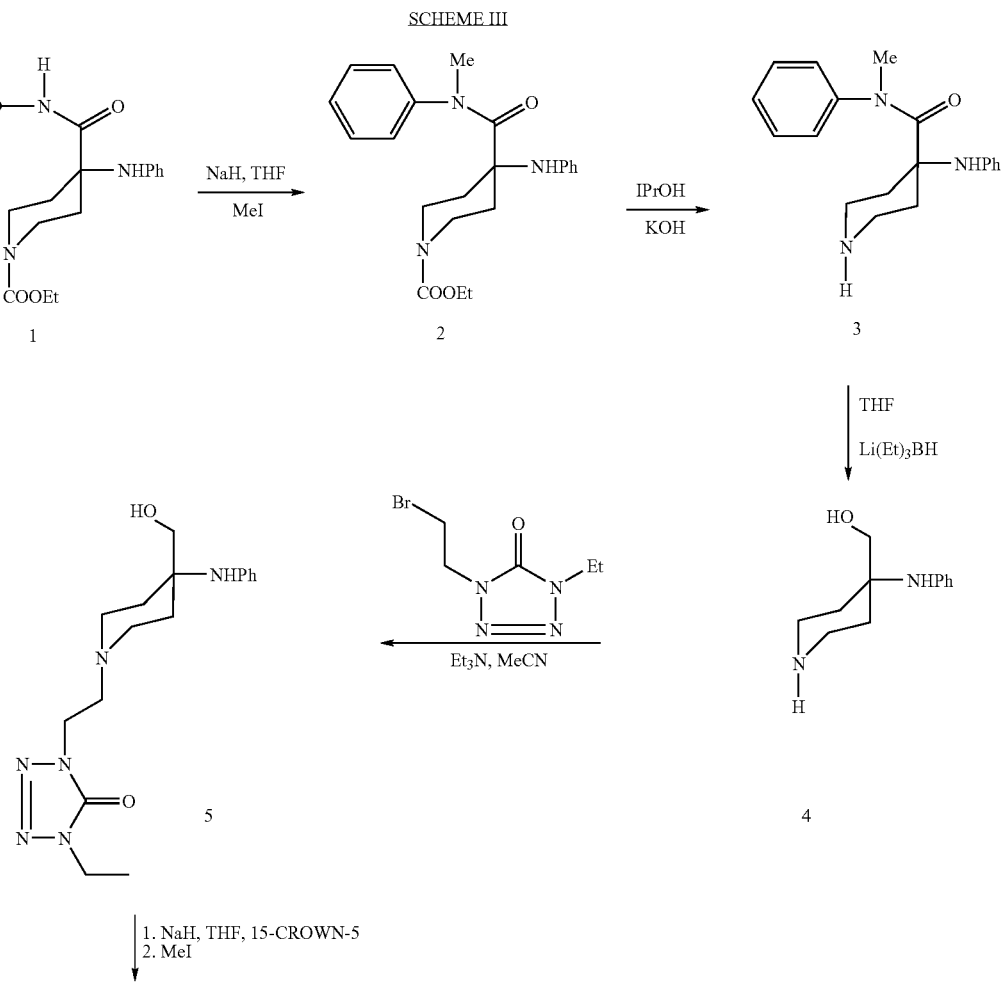

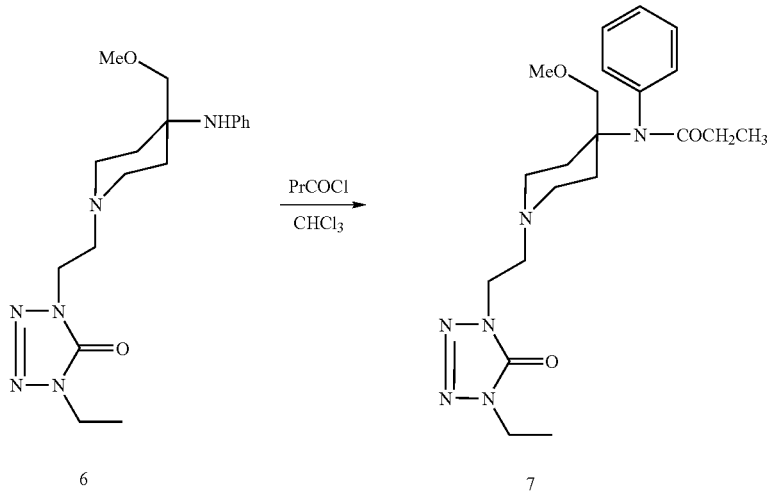

several other steps such as purifications, triturations and evaporations which are detailed in the procedures below.

Methods are also described for the synthesis of sufentanil. The first 4 steps of this method are identical to the above described method for synthesizing alfentanil. Then product 4 of Scheme III is subjected to three further reactions to produce sufentanil as shown in Scheme IV. The final three steps are the condensation with a mesylate (methanesulfonyl), conversion of an alcohol group to an ether, and condensation with propionyl chloride.

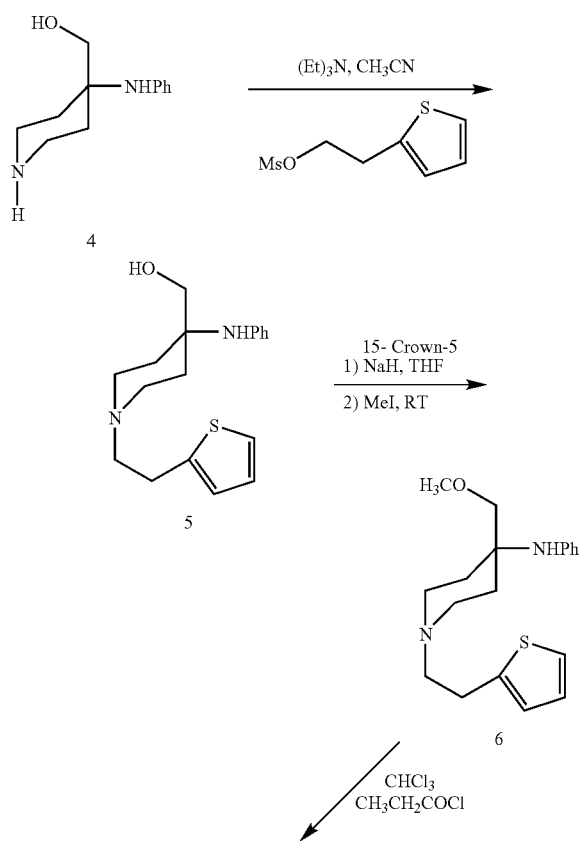

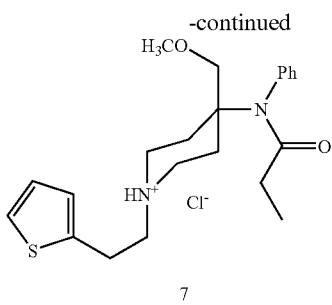

Finally, a scheme for the synthesis of remifentanil and analogs of remifentanil is set out.

DETAILED DESCRIPTION OF THE INVENTION

The present invention provides a method for preparing fentanyl derivatives.

In accordance with one embodiment of the present invention, a piperidine derivative is prepared by condensing a piperidone with a primary amine, such as aniline, so as to form a 4-amino-4-carboxyamino-piperidine.

In preferred embodiments, the ring nitrogen (N) of both the piperidone and the 4-amino-4-carboxyamino-piperidine includes a —COO—$(CH_2)_n$—$CH_3$ substituent, wherein n is an integer of from zero to about 10.

In particularly preferred embodiments, the piperidone is 1-carbethoxy-4-piperidone, and the 4-amino-4-carboxyamino-piperidine is 1-(carbethoxy)-4-(phenylamino)-4-piperidine carboxanilide, shown as formula 1 in Scheme III.

In preferred embodiments, the primary amine with which the piperidone is condensed is aniline. In particularly preferred embodiments, the piperidone is reacted with chloroform to form an intermediate epoxide, which epoxide is then reacted with the primary amine so as to form the 4-amino-4-carboxyamino-piperidine, in accordance with the following scheme.

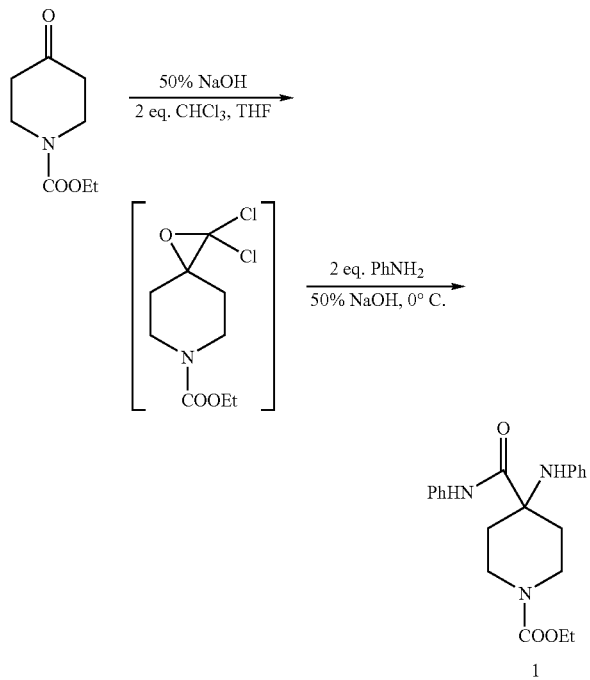

As can be seen in the scheme immediately above, the epoxide formed therein is a dichloroepoxide. In accordance with this embodiment, the epoxide is reacted with the aniline so as to form the compound of formula 1 above.

In accordance with one aspect of the present invention, the N of the carboxanilide is alkylated to form an N-alkylanilide derivative of the piperidine. In preferred embodiments the alkyl group is —(CH$_2$)$_n$—CH$_3$ where n is an integer from zero to four. In a most preferred embodiment the alkyl group is a methyl group. In a particularly preferred embodiment, the product formed is (1-carbethoxy)-4-(phenylamino)-4-piperidinecarbox-(N-methylanilide). This is shown as compound 2 of Scheme III.

In accordance with one aspect of the present invention, a 4-amino-4-carboxyamino-piperidine, in which the piperidine ring N includes a —COO—(CH$_2$)$_n$—CH$_3$ substituent, is hydrolyzed so as to remove the substituent attached to the ring N, and form a piperidine hydrolysis product. This ring N substituent can be hydrolyzed with an excess of alkali base, such as KOH, in an organic solvent such as isopropyl alcohol. In preferred embodiments, the piperidine hydrolysis product thus formed is 4-(phenylamino)-4-piperidinecarbox-(N-methylanilide) shown as product 3 in Scheme III.

In preferred embodiments, the above piperidine hydrolysis product is treated with a hydride to convert the carboxanilide to an alcohol. This is preferably performed in the presence of a super hydride, most preferably in the presence of lithium triethyl borohydride. In preferred embodiments, the resulting product is 4-(phenylamino)-4-(hydroxymethyl)piperidine, shown as product 4 in Scheme III.

In one embodiment of the invention, the alcohol is reacted with a sidechain group so as to attach a sidechain to the N of the piperidine ring. In a preferred embodiment, this sidechain is a tetrazole compound. In a more preferred embodiment, the tetrazole is an alkylated tetrazole. In a most preferred embodiment, the tetrazole is 1-{2-bromoethyl}-4-ethyl-1,4-dihydro-5H-tetrazol-5-one. The product formed in the most preferred embodiment is N-{1-{2-(4-ethyl-4,5-dihydro-5-oxo-1H-tetrazol-1-yl)ethyl}-4-(phenylamino)-4-(hydroxymethyl)piperidine}, shown as product 5 in Scheme III.

In one embodiment of the invention, the alcohol group present on the piperidine derivative is alkylated to yield an ether. The alkyl group is preferably a —(CH$_2$)$_n$—CH$_3$ where n is an integer from zero to 4. In a preferred embodiment the alkyl is a methyl. In a most preferred embodiment, the product formed is N-{1-{2-(4-ethyl-4,5-dihydro-5-oxo-1H-tetrazol-1-yl)ethyl}-4-(phenylamino)-4-(methoxymethyl)piperidine}, shown as product 6 in Scheme III.

In accordance with one aspect of the invention, alfentanil is synthesized by treating N-{1-{2-(4-ethyl-4,5-dihydro-5-oxo-1H-tetrazol-1-yl)ethyl}-4-(phenylamino)-4-(methoxymethyl)piperidine} with an acylating agent. In a preferred embodiment, the acylating agent is propionyl chloride. In a more preferred embodiment, the acylation step is performed using chloroform as the solvent, and in a most preferred embodiment, alfentanil hydrochloride is recrystallized from acetone.

Another aspect of the invention is a method of synthesizing a 1-{2-haloethyl}-4-ethyl-1,4-dihydro-5H-tetrazol-5-one from 1,2-dihaloethane and 1-ethyl-1,4-dihydro-5H-tetrazol-5-one. In a preferred embodiment this reaction is performed in the presence of a base selected from NaH, triethylamine or K$_2$CO$_3$ and in a solvent selected from tetrahydrofuran, acetonitrile or dimethylformamide. In a most preferred embodiment, the method is performed in the presence of triethylamine and in acetonitrile. Preferably the halide is Br. The tetrazole need not include a halide but can include any leaving group in place of a halide, e.g., a tosylate.

Yet another aspect of the invention is a novel method for the synthesis of sufentanil (N-{4-(methoxymethyl)-1-[2-(2-thienyl)ethyl]-4-piperidinyl}-N-phenylpropanamide). In a preferred embodiment, sufentanil is synthesized in a process which includes 4-(phenylamino)-4-(hydroxymethyl)piperidine as an intermediate, with sufentanil being made most preferably in a three step process from this intermediate.

In one embodiment of the invention, 4-(phenylamino)-4-(hydroxymethyl)piperidine is reacted with a mesylate of the formula R—(CH$_2$)$_m$—O-Ms wherein R is thienyl, preferably with 2-(2-thienyl)ethanol methanesulfonate, to attach the thienyl to the N of the pyridine ring.

In one embodiment of the invention, the thienyl substituted compound is alkylated at the alcohol group to yield an ether. The alkyl group is preferably a —(CH$_2$)$_n$—CH$_3$ wherein n is an integer from zero to four. In a preferred embodiment the alkyl is a methyl. In a most preferred embodiment, the product formed is N-(2-thien-2-ylethyl)-4-(phenylamino)-4-(methoxymethyl)piperidine.

In accordance with one aspect of the invention, sufentanil is synthesized by treating the N-(2-thien-2-ylethyl)-4-(phenylamino)-4-(methoxymethyl)piperidine with an acylating agent. In a preferred embodiment, the acylation step is performed using CH$_2$Cl$_2$ as the solvent and CH$_3$CH$_2$COCl as the acylating agent.

A further aspect of the invention are the novel compounds (1-carbethoxy)-4-(phenylamino)-4-piperidinecarbox-(N-methylanilide) and 4-(phenylamino)-4-piperidinecarbox-(N-methylanilide). These are shown as compounds 2 and 3 in Scheme 3. These compounds are useful for synthesizing both alfentanil and sufentanil.

In Scheme III, the reduction of compound 3 with super hydride gave the expected amino alcohol along with starting material 3 and N-methylaniline as shown by LC analysis. Mass spectra showed molecular ions corresponding (m/e=206) to the product and N-methylaniline (m/e=107). Since step 4 alcohol was obtained as a gum, attempts were made to convert it to the HCl salt and to purify it by solvent trituration or crystallization. Using either concentrated HCl or ethanolic solution of HCl to precipitate the amino alcohol as the hydrochloride failed. Extensive decomposition of the amino alcohol to a red tar was observed during these attempts. Even 5% aqueous acetic acid extraction of an ethyl acetate solution of this amino-alcohol resulted in complete destruction of this compound. The above results make clear that the amino alcohol is very labile to all acids. Furthermore attempts to separate the nonpolar impurities such as N-methylaniline by filtering over silica gel and eluting first with chloroform succeeded in removing these nonpolar impurities but the highly polar amino alcohol 4 was retained by the silica gel even after washing with 25% MeOH/CHCl$_3$. This amino-alcohol is a known metabolite of both alfentanil and sufentanil (Meuldermans et al., *Drug Metab. Dispos.* 15(6): 905–913 (1987)). This step 4 alcohol serves as a useful synthon for attaching any appropriate side chain and further elaborating to a fentanyl analog in 2 steps. Even though the step 4 alcohol has three reactive sites for alkylation, these being 1) the piperidine ring nitrogen, 2) the oxygen of the primary alcohol and 3) the nitrogen of the anilino group, the piperidine ring nitrogen is so much more nucleophilic than the other 2 centers that the side chain is attached at the desired piperidine ring nitrogen.

A further aspect of the invention is the synthesis of remifentanil and remifentanil analogs from compounds 3 and 4 of Scheme III.

EXAMPLE 1

Synthesis of Alfentanil by the Process Shown in Scheme III

Starting with 1-carbethoxy-4-piperidone, alfentanil is produced in about 16% yield in a 7 step reaction. These 7 steps are described here and again, in greater detail, in Example 6.

Step 1

As described in U.S. Pat. No. 5,489,689 which is incorporated herein by reference, 100 grams of N-carbethoxy-4-piperidone are treated to produce 98 grams of 1-(carbethoxy)-4-(phenylamino)-4-piperidinecarboxanilide. This product, shown as product 1 in Scheme III, is isolated as a white powder.

Step 2

It was established that 15-crown-5 was not required for this reaction due to the non-basic nature of the piperidine nitrogen which prevented quaternization side reactions with methyl iodide. Initial experiments with NaH in THF showed that the reaction of the anion with methyl iodide is best effected at room temperature. However, LC (liquid chromatography) monitoring showed that 12–16 hours of stirring at room temperature is essential for the almost complete disappearance of starting material. In order to assure a good isolated yield for this reaction it was necessary to use about 1.6 equivalents of 95% NaH for generating the amide anion and about 1.5 to 1.6 equivalents of methyl iodide. The excess methyl iodide did not cause any problems since no basic nitrogen was available for quaternization. The finally optimized procedure involved slowly adding a solution of the step 1 amide in THF to a stirred suspension of sodium hydride (1.6 equivalents) at ambient temperature. The tan cake (amide anion) was stirred at 50° C. for about 45 minutes and then cooled to room temperature and then methyl iodide was added slowly. After about 6 hours the thick cake slowly dissolved to give a fine suspension. An aliquot quench after 12–14 hours always showed less than 2% of starting product 1 by LC. The reaction was worked up after about 16 hours by removing THF and first quenching with methanol to destroy the excess NaH. The residue diluted with water and ethyl acetate and worked up to obtain a yellow gum. Trituration with cold ether gave product 2 as a white powder in 94% isolated yield which was 98–99% with less than 1% product 1. Use of several other solvents in the place of ether was not effective in obtaining product 2 as a white powder. The optimum yield for this reaction was 95% isolated with a LC purity of 96% with 1–2% of unreacted product 1. The upper limit of this impurity was set as 2%. The yield and assay data from four runs are tabulated below in Table 1.

TABLE 1

| Run # | Moles | Grams | Assay (LC) | % Yield |
|---|---|---|---|---|
| 1 | 0.23 | 85 | 97% | 94 |
| 2 | 0.052 | 19 | 98% | 90 |
| 3 | 0.226 | 83 | 93% | 98 |
| 4 | 0.21 | 77 | 97% | 95 |
| Average | 0.18 | 66 | 96.25% | 94.3 |

Step 3

Initial studies showed that product 2 can be decarbethoxylated with KOH (8–9 equivalents) in isopropanol, but this gave the desired compound 3 in only 70–75% isolated yield with partial cleavage of the amide resulting in N-methyl aniline. Reduction of this with super hydride or lithium tris diethyl amino hydride resulted in the desired product 4 alcohol.

However, conditions were developed which gave better yield of product 3 amide. This was achieved by refluxing with isopropanol (11 parts by volume) and KOH (6 equivalents) for 3 hours when LC analysis of an aliquot quench showed 85% product with only 2% of step 2 and no significant amount of the cleavage product N-methylaniline (<3%). Work up involves evaporating isopropanol and extracting into methylene chloride which on processing gave yellow semi-solid from which pure product 3 was obtained as a white powder by triturating with cold ether. Product 3 was isolated in 85–87% yield with an LC purity of 98%. This material was reduced with 5.5 equivalents of super hydride to give product 4 alcohol in high LC purity. It was also found that LC analysis was required for step 3 reaction monitoring due to the thermal degradation of step 3 amide at the GC injection port.

As a representative example for this step, full details of a large scale run are as follow. Starting with 78 grams of product 2, KOH (6 equivalents, 70 grams) and isopropanol (840 mL) were refluxed under nitrogen for 3 hours. The isopropanol was removed and the product was extracted with methylene chloride yielding 65 grams of yellow gum (LC=88%). This with triturated with ether yielding 56 grams (88% yield) of a white powder (LC purity=98%). The LC data representing the kinetics for this N-decarbethoxylation are shown in Table 2.

TABLE 2

| Time in Minutes | % Product by LC | % Step 2 Starting Material by LC |
|---|---|---|
| 40 | 39.4 | 51.5 |
| 80 | 75.5 | 15.4 |
| 120 | 91.5 | 3.6 |
| 160 | 93.4 | 2.6 |

The product 3 amide, although obtained as a white powder with 98% LC purity, was found to contain traces of isopropanol by NMR. Because isopropanol destroys the super hydride used in the next step, this powder was submitted for % weight of isopropanol by GC. GC results showed 7.6% isopropanol and 0.14% dichloromethane. This calculates to about 4.2 grams (73 millimoles) of alcohol in 56 grams of product 3. This required the use of 73 millimoles (73 ml) of 1 M super hydride in THF in excess of the theoretical needed for the reduction. This GC assay for isopropanol is essential and was incorporated in the final process. The yield and assay data from four runs are tabulated below in Table 3.

TABLE 3

| Run # | Moles | Grams | Assay (LC) | % Yield |
|---|---|---|---|---|
| 1 | 0.21 | 82 | 97% | 75 |
| 2 | 0.20 | 80 | 98% | 77 |
| 3 | 0.198 | 76 | 97% | 85 |
| 4 | 0.11 | 42 | 96% | 84 |
| Average | 0.18 | 70 | 96% | 80.25 |

Step 4

Direct conversion of product 2 amide to product 3 alcohol with super hydride was initially attempted but gave an overall isolated yield of 70% for the crude product with a GC purity profile of 78–80% product, 10–12% of an impurity with m/e of 248 and traces of product 2 and product 3 whereas LC showed only 30% product along with 45% N-methylaniline and considerable amount of unknown impurities (20–25%) of the desired product and therefore this scheme was abandoned. However, super hydride reduction (5.5 equivalents of 1 M super hydride in THF at room temperature for 24–36 hours) of product 3 gave after aqueous hydrolysis and 30% hydrogen peroxide oxidation (3 equivalents) to decompose the triethyl boranes the desired amino-alcohol in 75–78% isolated yield. The LC profile showed 51% product with only 0.54% starting material and the cleavage product N-methylaniline (47%) along with an impurity of less than 2%. The impurity is:

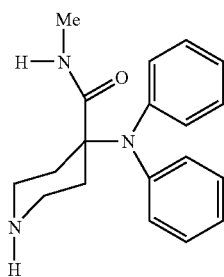

It was found that after the workup of the super hydride reduction, extracting the crude solution of product 4 alcohol in methylene chloride with water selectively transfers about 6–8% of pure product 4 alcohol into the aqueous layer since back extraction of the aqueous layer with chloroform gave, after removal of chloroform, product 4 alcohol in almost 90% LC purity. All of the N-methylaniline and the major impurity is removed by this process. This method however is not practically feasible to isolate the product since further water extractions of the methylene chloride solution transferred only about 5% of the total content. It was later discovered that the super hydride reduction is best worked up by quenching with the calculated amount of water and then with aqueous NaOH (2 equivalents) followed by dropwise addition of 30% hydrogen peroxide (3 equivalents) at ice bath temperature (see Example 6 below). The mixture is then stirred at 50° C. for 1 hour. THF is then evaporated and worked up with methylene chloride and water. Evaporation of methylene chloride gave a crude yellow oil which was redissolved in methanol (2 times by volume) and then evaporated at 50° C. under vacuum. This procedure removes the last traces of methylene chloride and THF as well as some of the N-methylaniline. GC analysis showed 22% by weight of N-methylaniline and LC showed 51% product and 39% N-methylaniline along with the 3% rearranged impurity and 0.9% starting material. This was used as such for the next step. The yield and assay data from four runs are tabulated below in Table 4.

TABLE 4

| Run # | Moles | Grams | Assay (LC) | % Yield |
|---|---|---|---|---|
| 1 | 0.15 | 39 | 51% | 71 |
| 2 | 0.16 | 42 | 55% | 72 |
| 3 | 0.164 | 41 | 44% | 62 |
| 4 | 0.09 | 23 | 42% | 70 |
| Average | 0.141 | 36.2 | 48% | 68.75 |

Step 5

Alkylation of product 4 alcohol with the side chain bromide (1.2 equivalents) in acetonitrile, or preferably in propionitrile because of its higher boiling point, (10 times by volume) containing 1.8 equivalents of triethylamine was complete in 3–4 hours reflux time (LC indicated 80:3 ratio for the product and starting material). Workup involved removing acetonitrile or propionitrile and adding dilute aqueous ammonium hydroxide and ethyl acetate. Initial studies indicated that extraction of the crude product 5 alcohol from the ethyl acetate extract using calculated amount of 1 N HCl resulted in obtaining product 5 alcohol with 75% LC purity leaving most of the N-methylaniline and all of the neutral side chain impurities in the ethyl acetate layer. When this was repeated with 10% acetic acid (3 equivalents) it was found that all of the N-methylaniline and side chain impurities along with most of the other nonbasic impurities stayed in the ethyl acetate layer. The aqueous acidic layer when basified with NH₄OH gave the product 5 alcohol in 84% LC purity. Workup was further modified to isolate product 5 alcohol in 93–95% LC purity. In early work the crude alcohol was filtered over silica gel (7 times by weight) and eluted first with chloroform (to remove any N-methylaniline and nonpolar impurities) followed by 5% MeOH/CH₂Cl₂ gave product 5 alcohol as a yellow 2um with 93–95% LC purity with only 2% of the polar impurity. This procedure was repeated for several runs in the range of 5 grams to 25 grams with consistent results. This gun was used for the next step after dissolving in THF and evaporating to dryness to remove the last traces of methanol and methylene chloride. Typically less than 0.02% by weight of methanol is detected by GC. Further elution of the silica gel with 8–10% MeOH/CH$_2$Cl$_2$ gave 5–8% of a yellow gum which was enriched in the impurity (25%) resulting from the alkylation of product 4 alcohol with the O-alkylated side chain. The kinetics of this step 5 alkylation were monitored by LC and are tabulated in Table 5.

More recent work shows that the purification step of filtering the crude alcohol over silica gel is unnecessary and the crude alcohol can be taken forward as is to Step 6.

TABLE 5

| Time in Minutes | % Step 4 (Starting Material) | % Step 5 (Product) |
|---|---|---|
| 30 | 13 | 28 |
| 60 | 10 | 30 |
| 90 | 9 | 40 |
| 120 | 6 | 43.5 |
| 180 | 5 | 45.2 |

In all runs 3–4 hours of reflux was sufficient since further heating did not result in any higher % of product by LC. This 45% LC area for the product is a high number considering that unreacted N-methyl aniline is still present in the reaction mixture (40–45%). The yield and assay data from four runs are tabulated below in Table 6.

TABLE 6

| Run # | Moles | Grams | Assay (LC) | % Yield |
|---|---|---|---|---|
| 1 | 0.12 | 19 | 91% | 46 |
| 2 | 0.013 | 2.5 | 93% | 55 |
| 3 | 0.025 | 3 | 94% | 41 |
| 4 | 0.075 | 10.8 | 95% | 43 |
| Average | 0.058 | 8.8 | 93.25% | 46.2 |

Step 6

This step was done with the above 91% pure product 5 alcohol or preferably with the crude alcohol by using the optimum conditions developed for this reaction (1.55 equivalents of NaH and 1.15 equivalents of methyl iodide) to give the crude product 6 in 84% isolated yield with an LC purity of 93%. Conversion of 0.5 grams of this to the HCl salt in ether gave a fine white powder with LC purity of 94%. Since the conversion to the HCl salt did not result in much higher LC purity, the crude free base (LC purity of 93%) was used as such for the next step.

The optimum conditions involve adding the methanol free product 5 in THF/15-crown-5 to a suspension of 95% NaH (1.55 equivalents) in THF/15-crown-5 at 30° C. under a nitrogen blanket. After bubbling stopped (10 minutes), the mixture was heated to 50–55° C. for 20 minutes to complete alkoxide formation. After cooling to ambient temperature, methyl iodide (1.15 equivalents) was added. After 30 minutes, work up by evaporating THF and diluting with water and ethyl acetate gave a crude brown gum in 89% isolated yield with an LC purity of 85% and less than 1% starting material. In early work, this was filtered through 7 times its weight of silica gel and first eluted with methylene chloride to remove non-polar impurities and then with 2% methanol/methylene chloride to get product 6 as a yellow gum in 84% isolated yield and 93% LC purity. Later work showed that this filtration through silica gel is unnecessary and it is preferably not used. This was used as such for the next step after dissolving in THF and evaporating to dryness to remove the last traces of methanol. The % methanol was determined by GC and found to be less than 0.1%. This procedure is necessary to ensure that propionyl chloride is not destroyed by any methanol present in the sample. It was also found that the optimum conditions involved using about 7 times volume of THF for every gram of product 5 charged and about 20% by volume of 15-crown-5 (about 1.5 times by volume of product 5 charged). The data from 4 runs are shown in Table 7.

TABLE 7

| Run # | Moles | Grams | Assay (LC) | % Yield |
|---|---|---|---|---|
| 1 | 0.06 | 17.8 | 93% | 84 |
| 2 | 0.008 | 2.3 | 95% | 79 |
| 3 | 0.054 | 15 | 91% | 78 |
| 4 | 0.030 | 8.1 | 92% | 80 |
| Average | 0.038 | 10.8 | 92.75% | 80.25 |

When ether was used instead of ethyl acetate for extracting the product from the crude reaction mixture it was found that a considerable amount of product was lost in the aqueous layer. The optimum ratio of NaH and methyl iodide was very important since excess methyl iodide will cause quaternization of the nitrogen. Furthermore this ratio always has given less than 1% starting material and therefore LC monitoring is not necessary. It is also important that the reaction be worked up no later than 30–45 minutes after addition of methyl iodide.

Step 7

Initially the reaction was conducted in methylene chloride as per the sufentanil process protocol (U.S. Pat. No 5,489, 689). However, even after 2–3 hours at 35° C. 3–5% step 6 remained. However, when product 6 free base was dissolved in chloroform and treated with propionyl chloride (1.6 equivalents) for 2 hours at 50° C. followed by an aqueous ammonium hydroxide workup, crude alfentanil free base was obtained as a yellow gum in 92% isolated yield and with 93% LC purity with about 1% of product 6. Conversion of this to the HCl salt in ether gave 99% isolated yield of alfentanil HCl with 96% LC purity. Alfentanil hydrochloride with an LC purity of 100% was obtained by recrystallizing from acetone (3 times by volume). Alfentanil hydrochloride is a white powder which appears to be much more stable in air than is sufentanil citrate. Many other solvents for recrystallization, including water, methanol, ethanol and isopropanol, were not suitable since the HCl salt was freely soluble in all of these. Recrystallization from acetone gave alfentanil HCl as a white powder in 78% isolated yield and with 100% LC purity. This appears to be the optimal condition for this final step.

This batch of alfentanil hydrochloride with an LC purity of 100% was dried for 2 hours at 45° C. and was submitted for determination of GC % of volatiles (acetone, ether and methylene chloride). The results are tabulated in Table 8.

TABLE 8

| Volatile | GC Result in PPM | GC Result as % |
|---|---|---|
| Acetone | 1760 | 0.176 |
| Ether | 170 | 0.017 |
| Methylene Chloride | None | None |

From this it is clear that alfentanil hydrochloride unlike sufentanil citrate (which typically even after 20 hours drying under vacuum at 50° C. gave 0.6 to 0.8% acetone) can be dried under mild conditions. None of the batches made so far appears to absorb water and melt even after exposing them to air. This is also in sharp contrast to sufentanil citrate. It was found that various ratios of acetone and other solvents such as THF, alcohols, ether, ethyl acetate and methylene chloride when used gave either no crystals or gave a product with a lower LC purity (96–99%). Thus it was concluded that acetone is the ideal solvent for recrystallization of alfentanil HCl even though the recovery yield was only 76–80%. Analysis of the mother liquor by LC showed that it had 62% alfentanil along with enriched amounts of product 6 and another nonpolar impurity. However another recrystallization of the mother liquor from acetone gave less pure product (about 88% by LC). It was necessary to remove most of the nonpolar impurity from the mother liquor by filtering through 8–10 times by weight of silica gel and first eluting with methylene chloride. Further elution with 2% methanol/methylene chloride gave crude alfentanil free base which when converted to the HCl salt and recrystallized from acetone gave another 8–10% yield of pure alfentanil HCl. This procedure could be incorporated for the rework of alfentanil HCl in the process.

Another area of investigation was the search for the ideal solvent to precipitate the hydrochloride salt from the free base. It was again found that the best procedure is to dissolve the free base in ether, add a slight molar excess of 1 M HCl in anhydrous ether (obtained from Aldrich in 1 liter bottles) yielding the HCl salt as a sticky solid precipitate. Ether is removed and the residue is recrystallized from acetone. When the free base was dissolved in ethanol or methanol and a HCl solution in methanol or ethanol was used, the HCl salt formed was too soluble in alcohol to precipitate. Even after removing the alcohol, acetone crystallization did not deposit any crystals even after cooling for several days. This is most likely due to traces of alcohol remaining which prevent alfentanil HCl from precipitating.

Three more batches of alfentanil hydrochloride (1–5 grams) with an LC purity of 99.2 to 100% were dried for 2 hours at 45° C. and submitted for determination of % volatiles (acetone, ether and methylene chloride) by GC. The results are tabulated in Table 9.

TABLE 9

| Volatile | Batch 1 | Batch 2 | Batch 3 |
|---|---|---|---|
| Acetone | 0.64% | 0.2% | 0.49% |
| Ether | 0.29% | 0.4% | 0.16% |
| Methylene Chloride | None | None | None |

U.S.P. testing was conducted on 3 batches of alfentanil hydrochloride as prepared above. The results are shown in Table 10.

It was later found that the above step 7 procedure can be modified so that the HCl salt is not made from the isolated free base in ether but rather directly during the reaction itself. For this the product 6 ether (LC purity=93%) was dissolved in chloroform (6 times by volume) and stirred at room temperature while propionyl chloride (2 equivalents) was added in 1 minute. The temperature rose to 40° C. and the yellow solution was then stirred at 50° C. for 2 hours at which time LC showed about 1.5% of product 6. The solvents were removed at 50° C. and the residue stirred with acetone (4 times by volume) and then evaporated at 50° C. using a Buchi. The yellow residue was redissolved in warm acetone (3 times by volume) and kept in the freezer for 12 hours. The white powder that precipitated was filtered off and air dried. LC showed 97% alfentanil HCl with 0.8% product 6. This was reslurried twice in warm acetone (2 times by volume), cooled for 2 hours and filtered to get alfentanil hydrochloride as a white powder with LC purity of 99.2%. The isolated yield for this reaction was 78%. This was repeated on a large scale and from 18 grams of product 6 there were obtained 16.5 grams of alfentanil HCl as a white powder with LC purity of 99.1%. A U.S.P. assay was done to confirm the purity of this sample.

TABLE 10

| Sample # | U.S.P. Test | Found | U.S.P. Limit |
|---|---|---|---|
| 4 (9 grams) | % Assay | 100.42 | 98–102% |
| | % Water | 3.02 | 4% |
| | Melting Point | 134° C. | 133–144° C. |
| | Residue on Ignition | 0.08% | 0.1% |
| 5 (3.5 grams) | % Assay | 99.67% | 98–102% |
| | % Water | 2.7% | 4% |
| | Melting Point | 133° C. | 133–144° C. |
| | Residue on Ignition | 0.06% | 0.1% |
| 6 (5 grams) | % Assay | 98.93% | 98–102% |
| | % Water | 2.84% | 4% |
| | Melting Point | 133° C. | 133–144° C. |
| | Residue on Ignition | Not determined | 0.1% |

The yield and data from four preparations are tabulated in Table 11.

TABLE 11

| Run # | Moles | Grams | Assay (LC) | % Yield |
|---|---|---|---|---|
| 1 | 0.039 | 9 | 99.3% | 65 |
| 2 | 0.028 | 7 | 99.4% | 60 |
| 3 | 0.02 | 6 | 99.5% | 58 |
| 4* | 0.009 | 0.9 | 100% | 24 |
| Average | 0.024 | 5.72 | 99.55% | 51.75 |

*Run 4 used product 6 material which was only 75% pure by LC and therefore extensive purification of product 7 free base was necessary before conversion to alfentanil HCl.

The noteworthy feature of this modified procedure is that the free base is not isolated and then converted to the hydrochloride in a solvent (thus eliminating aqueous workup and two isolation steps) and then recrystallized from acetone, rather alfentanil hydrochloride is isolated directly from the reaction flask without even an aqueous workup. The success of this procedure is solely due to the fact that conversion of product 6 to alfentanil HCl is almost quantitative in chloroform. Even more interesting is the fact that the piperidine nitrogen of product 7 (alfentanil free base) is acting as an excellent scavenger for HCl. This reaction can be conducted in acetone but complete conversion of product 6 was not possible even under forcing conditions (3 hours reflux) since LC showed about 14–16% unreacted product 6. The yield and assay data from two runs are tabulated below in Table 12.

TABLE 12

| Run # | Moles | Grams | Assay (LC) | % Yield |
|---|---|---|---|---|
| 1 | 0.048 | 16.5 | 99.2% | 78 |
| 2 | 0.0064 | 1.6 | 99.1% | 74 |
| Average | 0.0272 | 9.05 | 99.15% | 76 |

U.S.P. testing results on the 2 batches of alfentanil hydrochloride made by the modified step 7 procedure are tabulated in Table 13.

TABLE 13

| Sample # | U.S.P. Test | Found | U.S.P. Limit |
|---|---|---|---|
| 1 (1.5 grams) | % Assay | 100.11% | 98–102% |
| | % Water | 3.2% | 4% |
| | Melting Point | 134–135° C. | 133–144° C. |
| 2 (16.1 grams) | % Assay | 101.1% | 98–102% |
| | % Water | 2.93% | 4% |
| | Melting Point | 135–136° C. | 133–144° C. |

EXAMPLE 2

Side Chain Synthesis

Alkylation of 1-ethyl-1,4-dihydro-5H-Tetrazol-5-one with 1,2-dibromoethane (3 equivalents) in acetonitrile with triethyl amine (1 equivalent) as base is fast (1 hour). Excess halide is essential to minimize dimer formation. Crude isolated yield was 78–80% with GC purity of 85%. Up to about 10–11% of the isomer (O-alkylation) is also formed as evidenced by GC/MS study. It was hoped that less polar solvent such as THF will be used to minimize the extent of O-alkylation. Therefore several attempts were made to improve the yield for this reaction by reducing the amount of O-alkylation product formed. The results obtained with different bases and solvents are tabulated in Table 14. From these results it was concluded that triethyl amine/acetonitrile combination was the most desirable. The reaction is over after 1 hour of reflux. The reaction is:

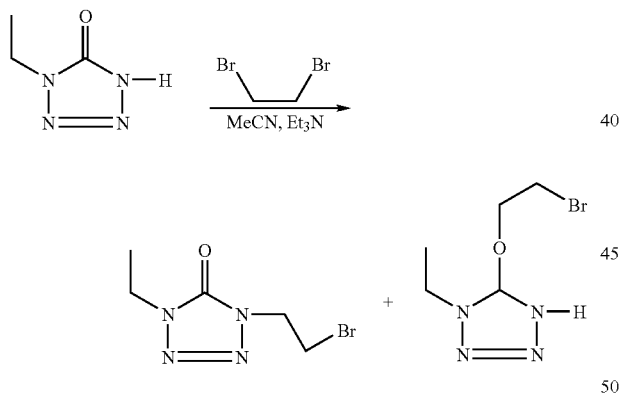

TABLE 14

| Base Used | Solvent | % Product | % O-alkylation | % Dimer |
|---|---|---|---|---|
| NaH | THF | 5 | 15 | — |
| Et₃N: | THF | 67 | 16 | 14 |
| Et₃N: | Acetonitrile | 84 | 10 | 5 |
| K₂CO₃ | Acetonitrile | 70 | 12 | 3 |
| Et₃N: | DMF | 74 | 23 | 2 |

In early experiments, the desired side chain product was isolated in 92–94% GC purity by filtering over silica gel (twice the weight of the crude product) and eluting first with hexane to remove the excess 1,2-dibromoethane and then methylene chloride to elute the product. Later work found a preferable method of removing the 1,2-dibromoethane. The side chain is not filtered through silica gel at all, rather the crude oil is taken up in isobutyl alcohol and an azeotropic distillation is performed. The 1,2-dibromoethane distills off together with the isobutyl alcohol leaving an oil which is used in step 5. This is performed by heating the product to 80° C., mixing with isobutyl alcohol and stripping solvent at 80° C. and a vacuum. This yields a free-flowing liquid which is used in step 5. The product is about 65% by weight the N-alkylation product.

It was also found that there is no need to separate the N-alkylation product from the O-alkylation product. The O-alkylation product is removed during steps 5–7 such that by the end of step 7 the O-alkylation product is almost completely absent.

EXAMPLE 3

Two major impurities in the process were isolated by preparative TLC. One of them was assumed to arise from the alkylation of product 4 alcohol with the O-alkylated side-chain impurity to give polar impurity 1 with retention time of about 7. This was confirmed by a combination of LC/MS and detailed NMR analysis (proton, carbon-13 (APT), HMQC and HMBC. The second one was thought to arise from the alkylation of unreacted product 3 intermediate with the side chain to give the nonpolar impurity 2 with retention time of about 10 min. 45 sec.

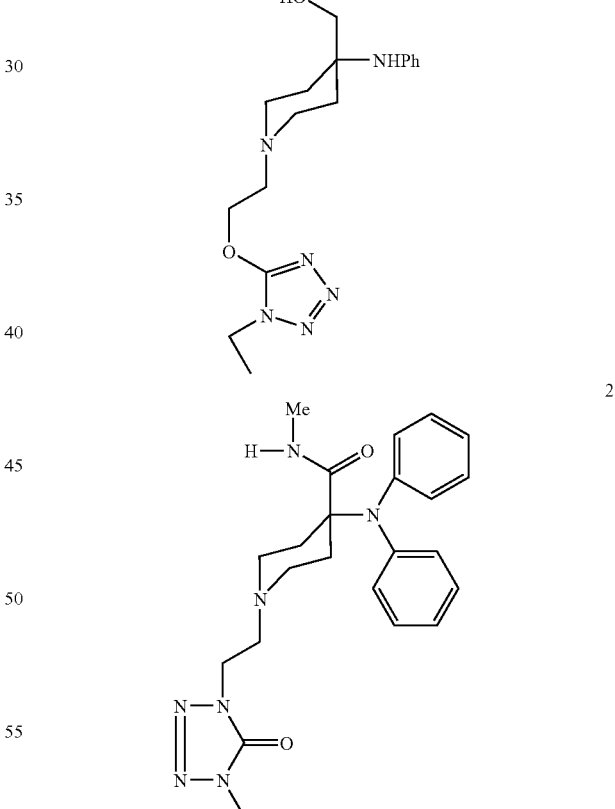

However, results from detailed NMR analysis indicate a rearranged product which has the same molecular weight as the one proposed earlier. Most likely 2 arises from alkylation of the rearranged amide 3 (arising from product 3 during Super-Hydride® reduction) with the side chain (Scheme V). This amide 3 once detailed NMR analysis indicate a rearranged product which has the same molecular weight as the one proposed earlier. This amide 3 once formed is not reduced by the Super-Hydride® since it is a secondary amide. Interestingly, this impurity is minimal (5–6%) as shown by LC if the amide is added to the Super-Hydride® slowly and appears to be the highest (15–18%) when Super-Hydride® is added to the amide in THF.

SCHEME V

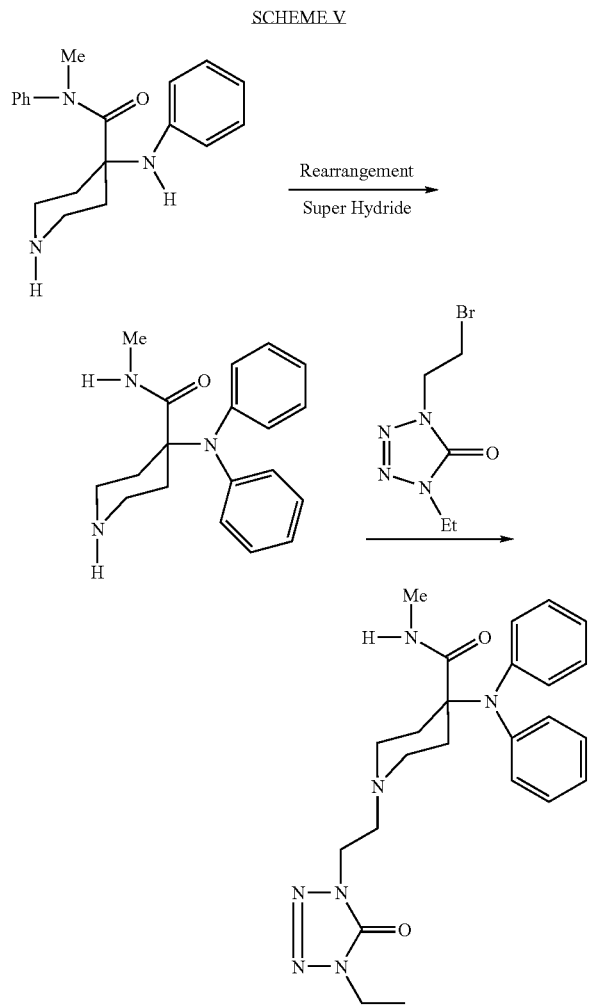

SCHEME VI

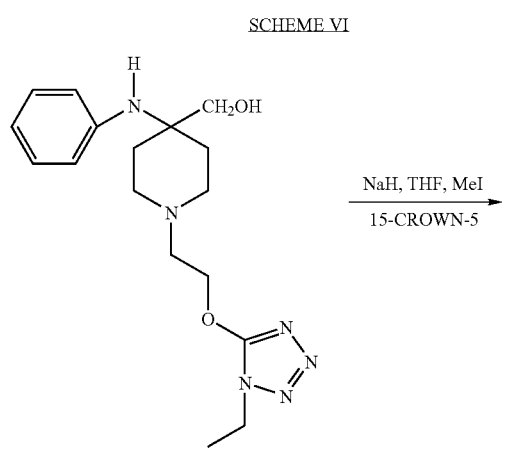

-continued

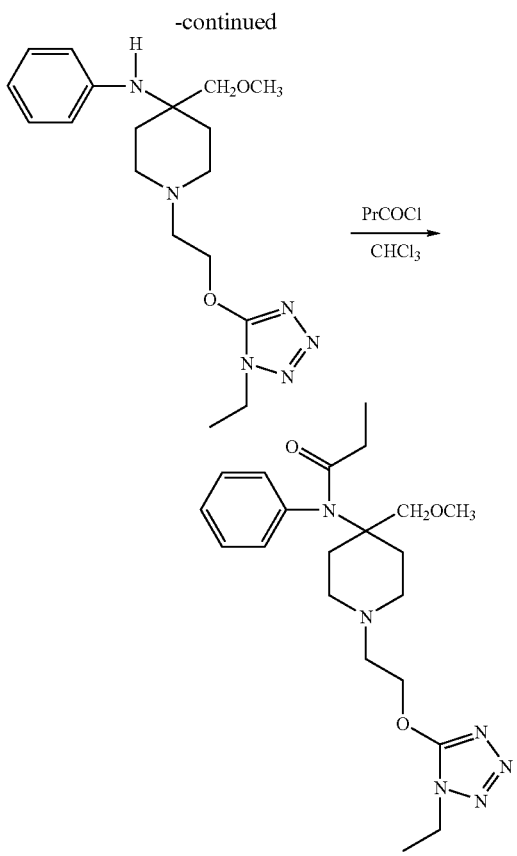

However, these are also almost completely removed (<0.2%) during the acetone recrystallization of the crude alfentanil hydrochloride.

EXAMPLE 4

Summary of the Process Yield

A summary of the process yield on a step by step basis is given below for a large scale run. The yield and LC purity profile of each step are shown in Table 15.

TABLE 15

| Substrate | Charge (grams) | Isolated Yield (grams) | LC Purity |
| --- | --- | --- | --- |
| N-carbethoxy-4-piperidone | 100 | 101 (47%) | 99% |
| 1 | 80 | 79 (95%) | 98% |
| 2 | 79 | 49 (76%) | 99% |
| 3 | 49 | 23 (72%) | 89%[a] |
| 4 | 23 | 19 (51%) | 91% |
| 5 | 19 | 17.4 (84%) | 93% |
| 6 | 17.4 | 16.2 (82%) | 99.2%[b] |

[a]The actual isolated weight of crude product 4 alcohol was 42 grams which contained an equimolar amount of thebyproduct N-methylaniline. The % by weight of N-methylaniline in the sample was calculated by GC analysis and was foundto be 38%. When this was subtracted from the 42 grams of crude product 4 alcohol isolated, this amounted to 23 grams ofproduct 4 alcohol with LC purity of 89% whereas the LC analysis of this crude sample showed 55% product, 34%N-methylaniline with 4.5% rearranged product and 1.2% starting material.
[b]Direct recrystallization of the crude residue from the reaction gave a white powder of alfentanil HCl.

Based on this run, the overall yield of alfentanil HCl from step 1 product calculates to be 16% based on obtaining 16.2 grams of pure alfentanil hydrochloride from 80 grams of product 1. This translates to 20.25 grams of alfentanil hydrochloride from 100 grams of product 1 or 202 grams from 1 kilogram of product 1.

EXAMPLE 5

Safety Considerations

Step 2 and step 6, both of which use sodium hydride and identical reaction conditions, require an inert atmosphere. Unfortunately, 50% NaH in mineral oil will not work for both steps if used as such. Therefore, the commercially available 95% NaH powder is used. Working with this highly reactive form of NaH requires extra care and adherence to all necessary safety backup procedures associated with the use of pyrophoric metal hydrides. For both these steps, substituting NaH with other bases gave no product.

Step 4 uses Super-Hydride® (lithium triethylborohydride) in THF which is available exclusively from Aldrich chemical company as a 1 M solution in THF. This reagent is not available commercially in the powder form or as a solution in toluene or any other solvent. This is the only reagent that will effect this transformation in good yield. Use of LAH (lithium aluminum hydride) gives a poor yield of the alcohol and is contaminated with several side products. Super-Hydride®, although a very reactive hydride, is more easily handled than THF solutions of LAH or LAH powder. No special precautions are necessary in handling this reagent except anhydrous reaction conditions and an inert atmosphere used for typical metal hydride reductions. The workup with water and 30% hydrogen peroxide converts all the triethylborane complexes to lithium borate salts and thus eliminates any fire hazard that triethyl borane would have posed during workup. Simple filtration removes the borate salts from the THF reaction mixture. Product 4 is directly isolated from the THF solution in high purity.

Steps 1, 3 and 5 require no special safety precautions except that a nitrogen atmosphere be maintained. These three steps are not expected to pose any problems during scale up. However, it must be mentioned at this point that any variations of the synthetic control parameters will result in lower yield.

Step 7 poses some safety concerns since alfentanil hydrochloride is formed in this step. Gloves, protective clothing and face mask must be worn by the worker at all points of this step including reaction monitoring, workup and purification. Alfentanil HCl is easier to handle than sufentanil citrate since it is free flowing and powdery and easily purified by crystallization from acetone and isolated as white crystals. Alfentanil hydrochloride being much less potent than sufentanil is not expected to pose any serious safety concern to the worker.

EXAMPLE 6

Detailed Steps of Synthesis of Alfentanil

Step 1: Preparation of 1-(carbethoxy)-4-(phenylamino)-4-piperidinecarboxanilide (product 1)

To a stirred ice cooled solution of N-carbethoxy-4-piperidone (100 g, 0.58 mole) in THF (250 mL) in a 3-necked flask under nitrogen was added chloroform (138 g, 1.16 mole) followed by benzyl triethyl ammonium chloride (4 g, 5% cat.). A cold solution of sodium hydroxide (24 g, 0.6 mole) in water (25 mL) was added in the course of 15 minutes via a dropping funnel fitted on one neck of the flask so that the inside pot temperature stayed between 5–8° C. At the end of the addition of the NaOH, aniline (107 g, 1.16 mole) was added during a 10 minute time period. After 5–10 minutes aqueous sodium hydroxide (56 g, 1.4 mole) in 56 mL water was added slowly over a 10 minute time period. After stirring at 5° C. for another 6–7 hours, the mixture was stirred overnight at 10–12° C., warmed to room temperature and worked up by stirring with a large excess of water (800 mL) and ethyl acetate (1 L) until a clear two phase system resulted. The organic layer was separated, washed with water (100 mL), 2 N HCl (2×50 mL), 10% aqueous $NH_4OH$ (40 mL) and was then dried. Evaporation of solvent gave a yellow viscous mass (150 g) which was about 86% product 1 by LC. Stirring the crude product with a minimum amount of cold ether (100 mL) gave, after filtration and drying, pure product 1 (102 g, 48% based on piperidone) as a white powder with a melting point of 159–160° C. $^1$HNMR: 8.95 (s, 1H), 7.55–6.65 (m, 10H), 4.15 (q, 2H), 3.90 (m, 2H), 3.10 (t, 2H), 2.30 (d of t, 2H), 1.90 (d, 2H), 1.20 (t, 3H). $^{13}$C NMR: 174.89, 173.20, 155.55, 143.16, 137.66, 129.56, 129.08, 124.54, 120.37, 119.98, 116.71, 61.58, 59.41, 39.29, 14.75. IR: 3357, 1684, 1498 and 1250 $cm^{-1}$. Mass spectra: 367(M+), 247.

Step 2: Preparation of (1-carbethoxy)-4-(phenylamino)-4-piperidinecarbox-(N-methylanilide) (product 2)

Product 1 (83 g, 0.225 mole) was dissolved in THF (250 mL) and added slowly via dropping funnel to a stirred suspension of 95% sodium hydride (10 g, 0.37 mole) in THF contained in a 3-neck-1-liter flask at ambient temperature under a nitrogen blanket. When the initial exotherm and frothing was over (10 minutes), the tan suspension was warmed to 50° C. for 45 minutes using a constant temperature heating controller. The thick tan cake was cooled to room temperature and methyl iodide (52 g, 0.37 mole) was added slowly so that the inside pot temperature did not rise above 32° C. A clear brown solution with a white precipitate resulted in about 3–4 hours. LC analysis showed about 11–12% of product 1. The mixture was stirred at ambient temperature for another 12 hours (LC typically shows less than 2% of product 1) and then most of the THF was removed using a rotary evaporator. The residue was quenched with methanol (2 mL) to destroy any excess NaH and then diluted with water (200 mL) and ethyl acetate (500 mL). The organic layer was separated, washed with water (50 mL), dried and the solvents were evaporated yielding a crude yellow gum. This was stirred with diethyl ether (80 mL) for 10 minutes and kept in the freezer for 2 hours. The thick precipitate was filtered and dried to obtain 82 grams (95%) of product 2 as a white powder with a melting point of 122° C. LC showed 99% purity. $^1$H NMR: 7.35–6.45 (m, 10H), 4.15 (q, 2H), 3.90 (m, 2H), 3.31 (s, 3H), 3.10 (t, 2H), 2.30 (d of t, 2H), 1.90 (d, 2H), 1.20 (t, 3H). $^{13}$C NMR: 173.12, 155.49, 143.12, 137,63, 129.50, 129.44, 124.47, 120.34, 119.86, 116.67, 61.49, 59.38, 39.26, 32.51, 30.95, 14.67. IR: 3357, 1684, 1498 and 1250 $cm^{-1}$. Mass spectra: 381(M+), 261.

Procedure for LC aliquot sample preparation: About 1 mL of the sample was withdrawn from the reaction mixture and quenched with about 2–3 mL of water and extracted with methylene chloride (2 mL). The methylene chloride solution was evaporated on a Buchi and the Rotavapor® and the residue was submitted for LC.

Step 3: Preparation of 4-(phenylamino)-4-piperidinecarbox-(N-methylanilide) (product 3)

A mixture of product 2 (82 g, 0.21 mole) and KOH (74 g, 1.32 mole) in isopropyl alcohol (820 mL) was refluxed under a slow stream of nitrogen for 3.5 hours. For the first hour, there was considerable frothing and carbon dioxide evolution. Therefore considerable care was taken to ensure that there was no excess heat applied during this period. After 3 hours of reflux, LC always indicated completion of this reaction (see Table 16 below for a plot of time vs. % product and starting material by LC). Typically, less than 4% of starting product 2 is detected at this point. The dark brown mixture was cooled to room temperature and most of the isopropanol was evaporated on a Buchi Rotavapor®. The residue was diluted with water (400 mL) and methylene dichloride (800 mL) and stirred for 5 minutes. The organic layer was separated, washed with water (2×30 mL), dried and the solvents were evaporated to give a brown viscous mass (90 grams). This was stirred with ether (120 mL) for 15 minutes and kept in the freezer for 4–6 hours. The thick yellow cake was filtered off, washed with a small amount (25 mL) of cold ether, and dried at 55° C. for 2 hours to get product 3 (54 grams, 83%) as a pale white powder with a melting point of 99–100° C. LC showed 98% purity. The percent weight of volatiles by GC was run for this powder and was found to contain 7.63% isopropanol and 1.25% ether. $^1$H NMR: δ 7.35–6.45 (m, 10H), 3.25 (s, 3H), 2.91 (t, 2H), 2.75 (t, 2H), 2.25 (t, 2H), 1.95 (d, 2H), 1.70 (s, 1H). $^{13}$C NMR: δ 173.73, 143.35, 137.70, 129.29, 128.89, 1214.14, 119.9, 116.64, 59.7, 41.61, 31.97, 25.35. IR: 3325, 1674, 1496, 1441 cm$^{-1}$. Mass spectra: 309 (M+), 189.

TABLE 16

| Time in Minutes | % Product | % Starting Material | % N-Methylaniline |
| --- | --- | --- | --- |
| 30 | 18 | 71 | 0.0 |
| 60 | 39 | 49 | 1 |
| 90 | 58 | 31 | 1.5 |
| 120 | 70 | 16 | 2 |
| 150 | 74 | 12 | 1.9 |
| 210 | 85 | 4 | 2.2 |

The original procedure for LC aliquot preparation was: About 1 mL of the sample was withdrawn and evaporated on a Buchi Rotavapor®. The residue was diluted with water (2 mL) and CH$_2$Cl$_2$ (2 mL) and the organic layer separated and evaporated on a Buchi and the residue submitted for LC analysis. Later LC analysis was performed by dissolving step 3 sample in methanol and shooting these dissolved samples neat.

Another 10% of pure product can be obtained from the mother liquor of the cold ether wash by reworking this solution (see Example 8 below).

Step 4: Preparation of 4-(phenylamino)-4-(hydroxymethyl)piperidine (product 4)

A solution of product 3 (47 g, 0.152 mole) in warm THF (100 mL) was added slowly in the course of 20–25 minutes via a dropping funnel to a stirred 1 M solution of lithium triethylborohydride in THF (900 mL, 0.9 mole) in a 2-liter-3-neck flask equipped with a mechanical stirrer under a nitrogen blanket. During the addition the pot temperature was maintained at 20–25° C. by using a water bath. The reaction is only mildly exothermic. The reaction may be monitored by LC and typically is complete after 24 hours. N-methylaniline (48%) and product 4 (47%) are the major components by LC along with less than 2% starting material. About 2–5% of a rearranged product is also typically seen by LC. The reaction mixture was cooled with ice and the calculated amount of water (25 mL) was first added dropwise to decompose the excess hydrides and complexes. After 10 minutes, 25% aqueous sodium hydroxide (100 g) was added followed by the dropwise addition of 30% hydrogen peroxide (300 mL, 3 equivalents) with ice cooling to oxidize the triethyl borane amine complexes (about 2 hours). The thick slurry that formed was stirred at 50° C. for 30 minutes and then the solvents were decanted and removed under vacuum at 50–55° C. until a cloudy suspension resulted. This residue and the original thick residue were stirred with CH$_2$Cl$_2$ (600 mL) and water (300 mL). The aqueous layer was extracted with methylene chloride (100 mL) and the combined organic layer was washed with water (50 mL), dried and evaporated to give yellow mass (43 grams). LC showed 42% product and 48% N-methylaniline. This was dissolved in methanol (150 mL) and evaporated under vacuum at 55° C. to give 39 grams of a yellow viscous gum. LC showed 51% product 4 and 39% N-methylaniline. $^1$H NMR: δ 7.30–6.80 (m, 5H), 3.65 (s, 2H), 2.85 (t, 4H), 1.85 (d of t, 2H), 1.62 (m, 2H. $^{13}$C NMR: 153.34, 137.40, 128.24, 126.74, 75.44, 64.34, 50.15, 41.72. IR: 3379, 3112, 1604, 1442, 1306, 849, 694 cm$^{-1}$. The percent of N-methylaniline by weight in this oil was determined by a GC method and was found to be about 22%. Based on the LC % of product 4 (51%) this crude oil (39 grams) was assumed to contain 21 grams of product 4 (66% yield).

The original procedure for LC sample preparation: About 1 mL of the reaction mixture was quenched with 3 drops of water and 0.3 g of 30% hydrogen peroxide was added dropwise at room temperature followed by 3 drops of 25% aqueous NaOH solution. The resulting solution was stirred with methylene chloride and the organic layer separated and evaporated on a Buchi and the residue was analyzed by LC. Later LC analysis was performed by dissolving step 4 sample in methanol and shooting these dissolved samples neat.

Step 5: Preparation of N-{1-{2-(4-ethyl-4,5-dihydro-5-oxo-1H-tetrazol-1-yl)ethyl}-4-(phenylamino)-4-(hydroxymethyl)piperidine} (product 5)

Product 4 and the sidechain bromide (see below) were dissolved in acetonitrile or preferably in propionitrile in a 1-liter flask. Then KI was added followed by triethyl amine. The mixture was stirred under nitrogen, gently refluxed (80–82° C.) and an aliquot analyzed by LC at 30 minute intervals. At the end of 4 hours, the maximum yield of product 5 was noted with only 4–5% of starting material left (see Table 17). The reaction mixture was cooled to room temperature and most of the acetonitrile evaporated (50° C.) under vacuum. Water (200 mL), ammonium hydroxide (20 mL) and ethyl acetate (500 mL) were added, stirred for 5 minutes, the organic layer was separated, washed with water (2×20 mL) and then extracted with 10% aqueous acetic acid (21 g of glacial acetic acid in 210 mL of water) (3 molar equivalents of product 4 charged). The aqueous acidic extract was basified with ammonium hydroxide to pH 11–12, extracted with methylene chloride (2×200 mL), washed with water (25 mL), dried and filtered. Evaporation of solvent gave 24 grams of yellow brown gum with an LC purity of 83% product and 4% polar impurity arising from O-alkylated side chain. The neutral ethyl acetate fraction had only 2% product along with N-methylaniline (48%) and side chain bromide (23%) and therefore was discarded. In early experiments, the crude product 5 gum was purified by dissolving in methylene chloride (10 mL) and applying to silica gel (160 g) packed on a fritted funnel. Initial elution with methylene chloride (350 mL) gave about 1 g of oil which had no product 5 by LC. Further elution with 5% methanol/CH$_2$Cl$_2$ (700 mL) gave 21 g (48%) of product 5 as a yellow gum. LC showed 93% purity. $^1$H NMR: δ 7.24–6.75 (m, 5H), 4.10 (t, 2H), 3.95 (q, 2H), 3.60 (s, 2H), 2.8 (t, 2H), 1.45 (t, 3H). Mass spectra: 347(M+1). Later experiments showed that the silica gel purification step is unnecessary and the crude product 5 can be taken forward as is to step 6.

TABLE 17

| Time in Minutes | % Product 4 | % Product 5 |
|---|---|---|
| 30 | 13 | 28 |
| 60 | 10 | 30 |
| 90 | 9 | 40 |
| 120 | 6 | 43.5 |
| 180 | 5 | 43.1 |

Step 6: Preparation of N-{1-{2-(4-ethyl-4,5-dihydro-5-oxo-1H-tetrazol-1-yl)ethyl}-4-(phenylamino)-4-(methoxymethyl)piperidine} (product 6)

Product 5 (21 grams, 70 millimoles) is dissolved in THF (100 mL) and evaporated (50° C.) under vacuum to constant weight. This procedure removed the last traces of methanol. (GC analysis for weight % of methanol typically shows less than 0.5%.) The residue was now dissolved in THF (70 mL) and added slowly via dropping funnel to a stirred suspension of 95% NaH (2.6 g, 97 millimole) in THF (80 mL) and 15-crown-5 (30 mL, 100 millimole) contained in a 3-neck-1-liter flask fitted with a stirrer, nitrogen inlet and thermometer at ambient temperature. The addition took about 4–5 minutes. When the initial exotherm and frothing was over (about 5 minutes), the tan suspension was warmed to 50° C. for about 30 minutes using a constant temperature heating controller. The mixture was cooled to ambient temperature and methyl iodide (10 g, 70 millimoles) was added via the dropping funnel at such a rate that the inside pot temperature did not rise above 38–40° C. A thick white precipitate formed immediately and after 30 minutes the inside pot temperature dropped to room temperature. (At this point LC analysis typically shows less than 1% of product 5.) The reaction mixture was transferred to a flask and THF was removed using a Buchi Rotavapor®. The residue was slowly quenched with methanol (1 mL) to destroy any excess sodium hydride and then diluted with water (100 mL) and ethyl acetate (300 mL). The organic layer was washed with saturated sodium chloride solution (2×20 mL), dried and the solvents were evaporated to give a crude product 6 as a brown gum (19.5 grams). LC showed about 86% desired product. In early experiments, the gum was dissolved in methylene chloride (10 mL) and applied to a packing of silica gel (140 g) on a fritted glass funnel. Initial washing with methylene chloride (300 mL) gave 1.5 grams of a yellow gum which was 45% product and 30% N-methylaniline by LC. Further elution with 2% methanol/methylene chloride (750 mL) gave 17.8 grams of a yellow gum after solvent removal. LC showed 93% product by LC with 3% polar impurity. The gum was dissolved in THF (100 mL) and then solvents were removed using Buchi Rotavapor® and then connected to vacuum pump for about 15 minutes. This procedure removed the last traces of methanol. The % weight of methanol by GC was typically less than 0.5%. $^1$H NMR: 7.2–6.80 (m, 5H), 4.05 (t, 2H), 3.95 (q, 2H), 3.30 (s, 5H), 2.80 (t, 2H), 2.60 (m, 4H), 1.95–1.65 (m, 4H), 1.45 (t, 3H). $^{13}$C NMR: 160.8, 154.5, 137.5, 128.5, 128.01, 67.44, 64.45, 63.04, 57.73, 51.05, 49.16, 40.15, 22.52. IR: 2812, 1601, 1700 cm$^{-1}$. Mass spectra: 360 (M+), 315. Later experiments showed that the silica gel step is unnecessary and the crude product can be taken directly to the next step without the silica gel purification.

Step 7: Preparation of N-{1-{2-(4-ethyl-4,5-dihydro-5-oxo-1H-tetrazol-1-yl)ethyl}-4-(methoxymethyl)-4-piperidinyl}-N-phenylpropanamide, hydrochloride, monohydrate (product 7)

Propionyl chloride (7.25 grams, 78 millimoles) was added to a solution of product 6 in chloroform (120 mL) at ambient temperature. A mild exotherm (40° C.) developed and analysis by LC at the end of 30 minutes showed 91% alfentanil with about 3% starting material. The mixture was then stirred at 50° C. for 2 hours. At the end of this time LC showed 92% product with 2% starting material (see Table 18). The mixture was stirred for another 30 minutes and then the solvents were stripped off at 50° C. using a Buchi Rotavapor®. The brown residue was dissolved in warm acetone (100 mL) and the solvents were evaporated to a brown viscous gum. This procedure was repeated again to get a yellow sticky powder. This residue was redissolved in warm acetone (50 mL) and slowly cooled to 0° C. for 12–16 hours. The precipitated HCl salt was filtered off, washed with cold acetone (3×5 mL), ether (20 mL) and air-dried to get 18.5 grams of a pale yellow white powder. LC showed 97% product (alfentanil HCl) and 1% product 6. Trituration with hot acetone (50 mL) and cooling for 2 hours gave alfentanil HCl (16.7 g, 81%) as a white powder with LC purity of 99.2% and a melting point of 134–135° C. (The reslurrying in hot acetone and cooling to 5° C. to precipitate the alfentanil HCl may have to be repeated if the LC results indicate lower than 99% purity.) $^1$H NMR: (CDCl$_3$, free base) δ 7.38–7.19 (m, 5H), 4.05 (s, 2H), 4.02 (t, 2H), 3.95 (q, 2H), 3.45 (s, 3H), 2.72 (t, 2H), 1.80 (q, 2H), 1.42 (t, 3H), 0.95 (t, 3H). U.S.P. assay was 99.85%. Percent water=0.3% and percent weight of volatiles by GC was 0.54% acetone and 0.15% ether.

TABLE 18

| Time in Minutes | % Product by LC | % Starting Material by LC |
|---|---|---|
| 30 | 91 | 3 |
| 90 | 92 | 2.4 |
| 120 | 93 | 2 |

The alfentanil HCl obtained from step 7 is recrystallized from an HCl solution to give the final product as follows. 60.5 g of alfentanil HCl is placed into 2.5× amount of water (151 g H$_2$O). To this is added 5.2 g activated charcoal and 10.4 g filtration aid (diatomaceous earth). Then 15.1 mL concentrated HCl is added (0.25 mL/g alfentanil HCl) and this is stirred until a slurry forms. This is followed by addition of 1 mL 1 N HCl/g alfentanil HCl (60.5 mL of 1 N HCl in this Example). This is chilled for over 2 hours and then filtered. The product is dried at approximately 40–55° C. until it is a constant weight. This final product is a monohydrate form of alfentanil HCl.

Preparation of the Sidechain Bromide (1-{2-bromo-ethyl}-4-ethyl-1,4-dihydro-5H-tetrazol-5-one 1-Ethyl-1,4-dihydro-5H-tetrazol-5-one (75 g, 0.65 mole), 1,2-dibromoethane (320 g, 1.69 mole, 2.6 equivalents), acetonitrile (200 mL) and triethylamine (68 g, 0.66 mole) were charged into a 2 liter reaction flask under nitrogen blanket and stirred using a mechanical stirrer. The mixture was then refluxed for about an hour. LC indicated completion of reaction within this time. Acetonitrile was evaporated (50° C.) using a rotary evaporator and deionized water (200 mL) and methylene chloride (500 mL) were added and the solution was stirred for 5 minutes. The phases were allowed to separate. The aqueous layer was separated and discarded. The organic phase was extracted with 100 mL of deionized water, and again the aqueous phase was separated and discarded. The organic phase was dried by stirring with 8–10 grams of anhydrous magnesium sulfate. The magnesium sulfate was filtered and washed with 10 mL of dichloromethane. The product containing organic phase was stripped until free of solvent (until almost constant weight) using a rotary vacuum evaporator (50° C. bath temperature). The bath temperature was then increased to 80° C. to remove the excess dibromoethane. The resulting residue was then taken up in 442 mL of isobutyl alcohol and then stripped until free of solvent using a maximum bath temperature of 80° C. and the best available vacuum to give a free-flowing oil. This azeotropic distillation removes any remaining dibromoethane. The oil is approximately 65% by weight N-alkylation product.

EXAMPLE 7

| HPLC Conditions | |
|---|---|
| A) Steps 1 and 2 | |
| Column: | Phenomenex Prodigy 5 C8, 250 × 4.6 mm, column temperature = 45° C. |
| Mobile Phase: | Isocratic, 70:30 MeOH:$H_2O$ |
| Flow Rate: | 1.5 mL/minute |
| Injection Volume: | 10 μL |
| Detector: | 220 nm |
| B) Steps 3–7 | |
| Column: | Phenomenex Prodigy 5 ODS-2, 150 × 4.6 mm, column temperature = 50° C. |
| Mobile Phase: A: | Milli-Q water with 1 mL/L concentrated $H_3PO_4$, pH to 6.0 with NaOH solution |
| B: | Acetonitrile |
| Gradient: | 10% to 80% B over 15 minutes, hold to 20 minutes, return to initial at 21 minutes, 5 minutes equilibration, (gradient controller gradient #3) |
| Flow Rate: | 2.0 mL/minute (normal initial pressure 2900 to 3100 using HPLC System #4) |
| Injection Volume: | 10 μL |
| Detector: | 220 nm |
| C) Sample Preparation | |

1) All samples are diluted in methanol
2) Powders are prepared at approximately 1–2 mg/mL
3) Oils are prepared the same as powders, estimate the concentration
4) Aqueous phase or acetone mother liquor samples, dilute 1:1 with methanol
5) If main peak is off-scale, dilute and reshoot
Report area percent values.

EXAMPLE 8

Rework Procedures

There are two instances where rework is necessary to improve the overall yield of the process.

A) Synthesis of Product 3

It is almost always necessary to recover the intermediate from the synthesis of product 3 from its mother liquor since about 20% by weight of crude product with an LC purity of 54–58% is usually detected in the ether mother liquor from product 3 purification. The major impurities are the non-basic product 2 (14–26%) and N-methyl aniline (15–20%). Since product 3 is much more basic than these two impurities an efficient separation is achieved by acid extraction of the crude mother liquor from ethyl acetate. The procedure is as follows. The crude step 3 mother liquor is concentrated and dissolved in ethyl acetate and then extracted with 3 molar equivalents of 10% aqueous acetic acid. The aqueous acidic layer is basified to pH 11 with ammonium hydroxide and extracted with ethyl acetate. Evaporation gives a yellow gum which is triturated with an equal amount of cold ether to obtain the intermediate as a pale yellow powder. LC purity of this powder is typically in the range of 89–93%. The yield of recovered material is about 9–10% of the theoretical overall yield for this step. For instance 15 grams of crude gum from the mother liquor with an LC purity of 54% gave 7 grams of product 3 in 92% LC purity after this rework. This reworked product 3 is reduced separately with super hydride to give a batch of product 4 with almost the same purity and yield as the one obtained from the main batch of product 3 and therefore these two batches can be combined and used to make product 5.

B) Synthesis of Product 7

In step 7, Alfentanil hydrochloride is obtained directly from the reaction mixture by evaporation of the reaction solvent and replacing with acetone and recrystallizing from this. Typically about 80% of alfentanil hydrochloride is obtained as a white powder in excess of 99% LC purity. The mother liquor from this recrystallization has a LC profile of 60–65% of product along with enriched amounts of product 6 and the major impurities. Attempts to obtain pure Alfentanil hydrochloride from this by two consecutive recrystallizations from acetone gave the product in only 98% LC purity at best. Titration assay showed only 95% alfentanil hydrochloride. Therefore a modified rework was deemed necessary. Conversion of this crude mother liquor to the free base gave a brown gum which was applied to 7 times its weight of silica gel and first eluted with methylene chloride (10 parts by volume) and then with 1% methanol:$CH_2Cl_2$ (about 40 times by volume). This eluate was concentrated to get a yellow gum which typically showed at least 85–90% alfentanil. Conversion to the hydrochloride with 1 M HCl in ether gave a white powder which was recrystallized from acetone to get alfentanil hydrochloride in excess of 99% LC purity. By this method about 4–5% additional alfentanil hydrochloride can be obtained.

EXAMPLE 9

Synthesis of Sufentanil

The synthesis of sufentanil is very similar to the above described synthesis of alfentanil. Beginning with N-carboxy-4-piperidone as with the alfentanil procedure, the first four steps of the process are identical so as to produce compound 4 of Scheme III. The process from the step 4 compound to sufentanil is shown in Scheme IV.

Step 5

The step 4 alcohol (4-(phenylamino)-4-(hydroxymethyl)piperidine) (231.4 grams) and a mesylate (2-(2-thienyl)ethanol methanesulfonate) (138.7 grams) are dissolved in acetonitrile in a 5-liter flask. Anhydrous potassium carbonate (7.7 grams) is added in one portion followed by 1.9 grams of KI and 115.4 grams of triethylamine. The mixture is stirred under nitrogen, gently refluxed (80–82° C.) and analyzed by LC at 30 minute intervals. At the end of 4 hours, a high yield of Step 5 product will be noted. This step 5 product is N-(2-thien-2-ylethyl)-4-(phenylamino)-4-(hydroxymethyl)piperidine. The reaction mixture is cooled to room temperature and most of the acetonitrile is evaporated using a Buchi Rotavapor® at 50° C. Water (1070 mL), ammonium hydroxide (107 mL) and ethyl acetate (2700 mL) are added and stirred for 15 to 20 minutes. Stirring is stopped and the phases are allowed to separate. The organic layer is separated, washed with water (2×107 mL) and then extracted with 10% acetic acid (870 mL followed by 186 mL). The organic phase is then washed with water (2×87 mL) and the aqueous phases combined with the aqueous acidic extracts. The combined aqueous phases are treated with ammonium hydroxide to a pH of 11–12 then extracted with methylene chloride (2×1070 mL). The organic phases are combined, washed with water (135 mL), dried over 28.2 grams of anhydrous magnesium sulfate, and filtered. The solvent is evaporated using either Buchi Rotavapor® or the rotary evaporator specified at 50° C. giving an amber oil that is dissolved in 56 mL of methylene chloride and chromatographed on a Biotage Flash 75L chromatography column with 1200 mL of methylene chloride followed by 2500 mL of 5% methanol in methylene chloride solution. The 5% methanol in methylene chloride fractions are combined and stripped until free of solvent using Buchi Rotavapor® or the rotary evaporator specified at 50° C. to give step 5 product as a yellow oil.

Step 6

The product 5 alcohol is converted to an ether just as done in step 6 of the alfentanil process described above. Here 21 grams of N-(2-thien-2-ylethyl)-4-(phenylamino)4-(hydroxymethyl)piperidine are used. The optimal conditions should be the same as with the alfentanil process. The product 5 alcohol is mixed with NaH and MeI in a solution of THF and 15-crown-5 ether at room temperature. This produces N-(2-thien-2-ylethyl)4-(phenylamino)-4-(methoxymethyl)piperidine (the step 6 product).

Step 7

The final step in the synthesis of sufentanil is to treat the step 6 product (16.3 grams) with propionyl chloride in chloroform as was done for the step 7 reaction of alfentanil as described above. The workup of the sufentanil product is similar to that for alfentanil.

EXAMPLE 10

Synthesis of Remifentanil

The synthesis of remifentanil known in the prior art uses the intermediate for the synthesis of carfentanil and is shown in Scheme VII. Although the yield in the earlier six steps is not high, the final step proceeds in high yield (90%). However, no other new synthetic route for remifentanil has appeared in the literature.

While developing a synthesis for alfentanil along the lines of a sufentanil process, it was found that the synthetic scheme was not suitable for alfentanil since the tetrazole side chain is easily reduced by the Super-Hydride® used in step 5 of the process. Subsequently a new synthesis was developed which incorporates the side chain after the Super-Hydride® reduction of the amide 2 to the alcohol 3 (see Example 1). This synthetic scheme was shown to be applicable to sufentanil itself (see Example 9). The key intermediate 4 shown in Scheme III is herein used for the rapid and easy synthesis of several analogs of remifentanil which may have better and more useful analgetic properties.

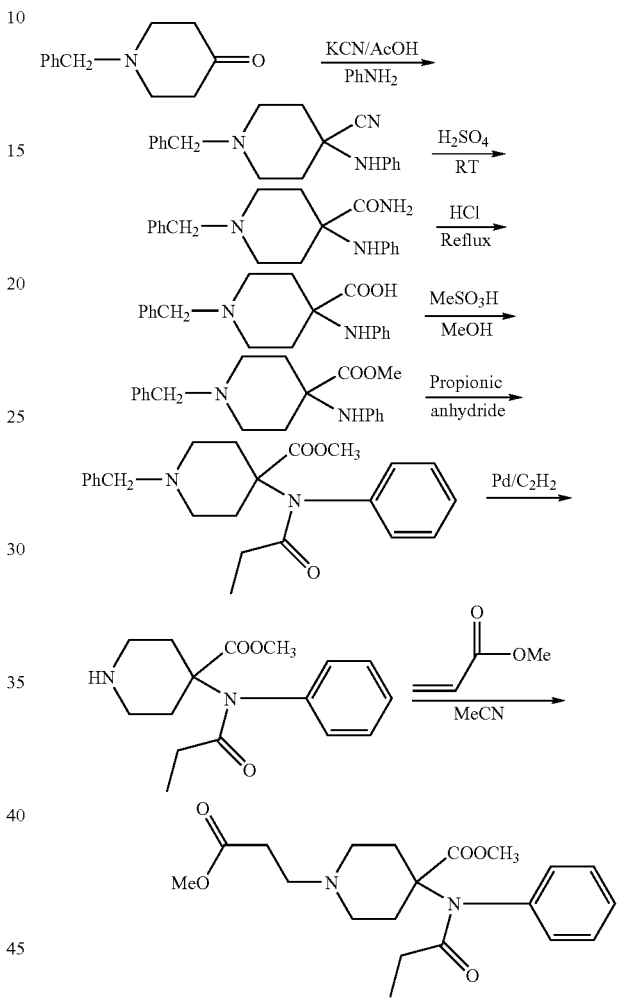

SCHEME VII

Alcohol 4 of Scheme III can serve as a useful synthon for attaching any appropriate side chain and for further elaborating to a fentanyl analog in 2 steps. Even though this intermediate 4 has three reactive sites for alkylation, i.e., 1) the piperidine ring nitrogen, 2) the oxygen of the primary alcohol and 3) the nitrogen of the anilino group, the piperidine ring nitrogen is so much more nucleophilic than the other two centers that the side chain is attached at the desired piperidine ring nitrogen.

A) Synthesis of Remifentanil Analogs from Intermediate 4

Intermediate 4 of Scheme III can be condensed with methyl acrylate in good yield (70–75%) by heating a mixture of intermediate 4 and 1.5 equivalents of methyl acrylate in acetonitrile for 3–4 hours. The adduct 5 (Scheme VIII) is obtained in high LC purity by a simple workup. The reaction of adduct 5 with excess propionyl chloride (2 equivalents) will yield the target remifentanil analog.

Scheme VIII

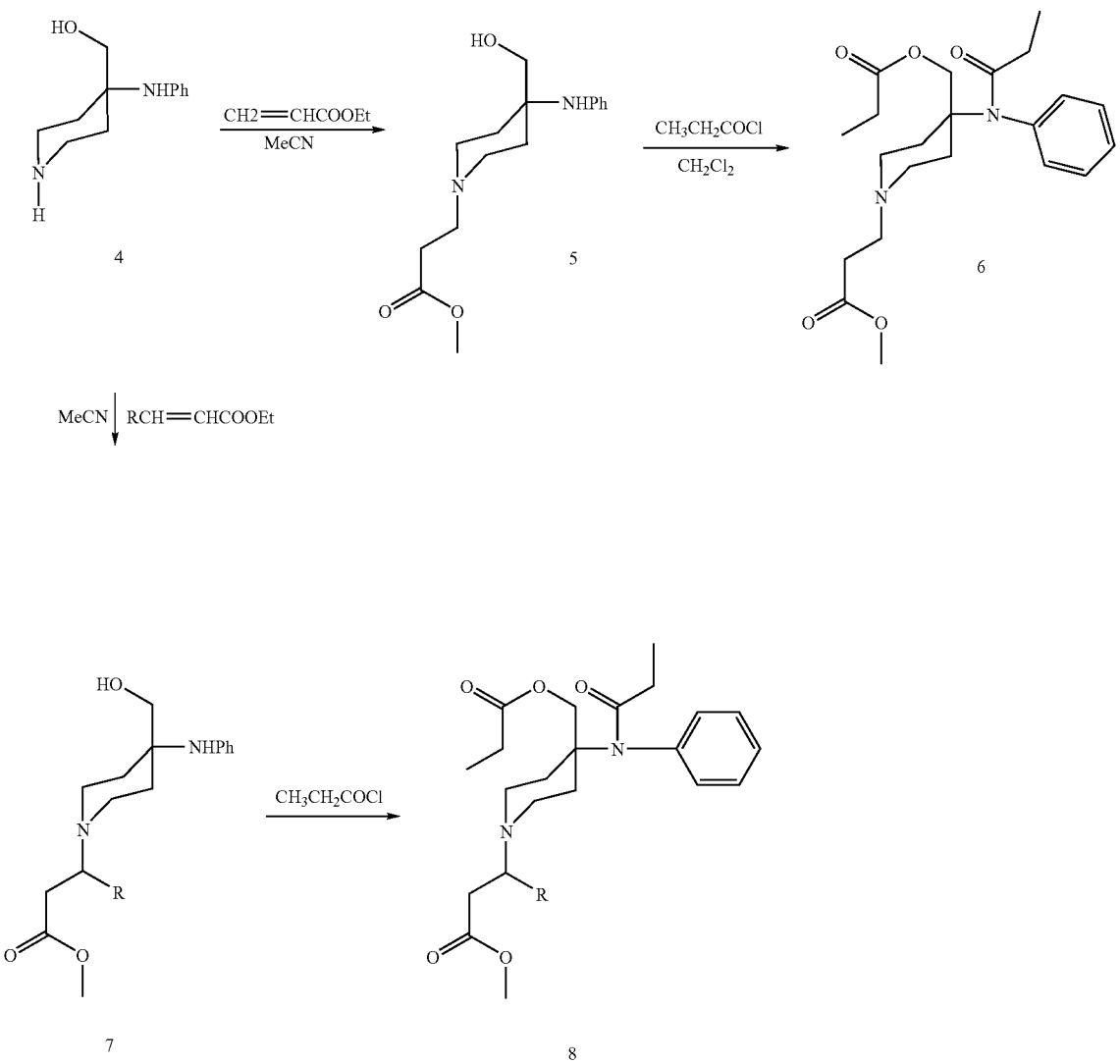

wherein R = Me or Ph.

Similarly, 4 can be condensed with methyl acrylate {R=Me} or methyl cinnamate {R=Ph} to yield 7 and subsequent reaction with propionyl chloride will yield target remifentanil analogs 8. As is evident, three potentially active analogs can be made from readily available acrylic esters.

Studies by Colapret et al. (*J. Med. Chem.* 32:968 (1989)) have shown that replacing the O-methoxymethyl substituent with 4-carboalkoxy esters and carbonates in the sufentanil series [thienylethyl side chain] and fentanyl series [phenethyl] gave compounds that were powerful analgesic agonists but with duration of action longer than desired (>6 minutes) (shown below). An examination of four active congeners in the N-phenethyl series reveals that the mere transposition of acetyl for propionyl groups imparts a decrease in analgesic activity (relative to fentanyl) with a 14-fold decrease in receptor binding affinity, but the two are similar to each

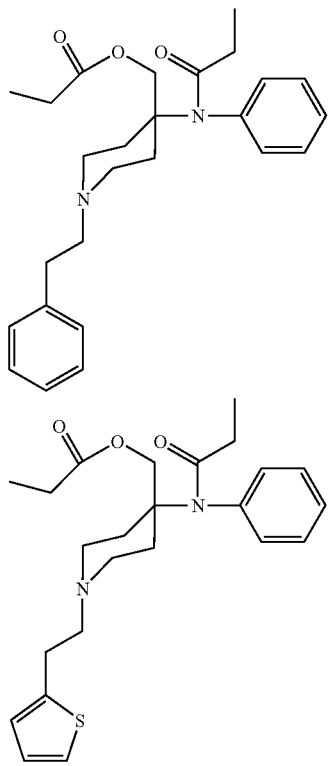

other in their anesthetic properties, i.e., same approximate potency and 5–6 minute duration. The same trend was also observed for the thienylethyl series with respect to their analgesic properties.

While the duration of action for many of the above compounds similar to the ones depicted above are longer than desired, it is reasonable to assume that appending alkyl esters onto the piperidine nitrogen instead of phenethyl or thienylethyl on these would yield potent analgetics with an ultrashort duration of action similar to remifentanil. To this end all of the target compounds outlined in Scheme VIII would serve as potential candidates for screening to see if they fulfill this requirement. Furthermore many other analogs of remifentanil for testing can be made from aminoalcohol 4 by a suitable choice of acrylic esters.

B) Synthesis of Remifentanil from Amide 3

A shorter synthesis of remifentanil itself is possible starting from amide 3 of Scheme III. Amide 3 can be alkylated with methyl acrylate to give a tertiary amide. Conversion of the tertiary amide to methyl ester can be effected by a one pot, two step sequence by first using excess potassium t-butoxide and 1 equivalent of water to hydrolyze the amide to the potassium salt of the acid and N-methylaniline followed by reaction of the acid salt with dimethyl sulfate in THF/15-crown-5 to yield the methyl ester. Finally, reaction with propionyl chloride would yield remifentanil.

The cleavage of the tertiary amide with excess potassium t-butoxide and one equivalent of water proceeds through first generation of one equivalent of hydroxide ion which adds to the amide to form a tetra-coordinated anion. The t-butoxide then removes a proton from this intermediate to generate a dianion, which undergoes spontaneous fragmentation to yield amide anion and a carboxylate anion. The above mechanism for the cleavage of tertiary amides to the acid has been studied on simple N-methyl amides derived from N-methyl aniline and has been reported to yield good yield of the desired product (Gassman et al., *J. Am. Chem. Soc.* 98:1275 (1976)). In situ conversion of the thus generated acid salts to the ester has not been reported butt use of THF/15-crown-5 should facilitate this transformation since 15-crown-5 is known to accelerate the rate of alkylation of acid salts even in the presence of a basic nitrogen.

Since many modifications, variations and changes in detail may be made to the described embodiments, it is intended that all matter in the foregoing description and shown in the accompanying drawing be interpreted as illustrative and not in a limiting sense.

What is claimed is:

1. A process for preparing alfentanil, the process comprising:

(a) reacting a piperidone compound having the formula

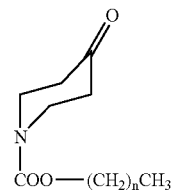

with chloroform to form a 4-dichloroepoxy-piperidine intermediate compound, said intermediate compound being reacted with aniline to form a 4-amino-4-carboxyamino-piperidine compound having the formula

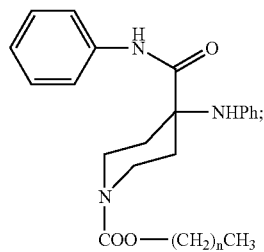

(b) alkylating the 4-amino-4-carboxyamino-piperidine compound to form an alkylated 4-amino-4-carboxyamino-piperidine compound having the formula

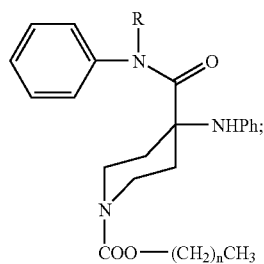

(c) hydrolyzing the ester group of the alkylated 4-amino-4-carboxyamino-piperidine compound to form a piperidine hydrolysis product having the formula

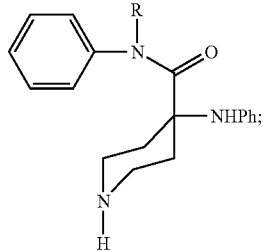

(d) treating said piperidine hydrolysis product with a hydride to produce a 4-hydroxymethyl-piperidine having the structure

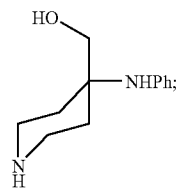

(e) reacting said 4-hydroxymethyl-piperidine with a haloalkyl-tetrazole so as to form an N-substituted tetrazole-piperidine product having the structure

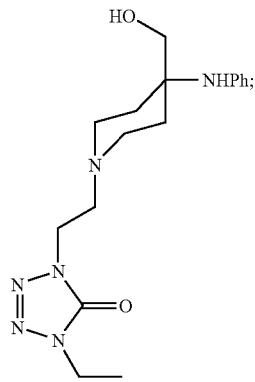

(f) etherifying said N-substituted tetrazole-piperidine product to form an alkoxymethyl-N-substituted tetrazole-piperidine product having the structure

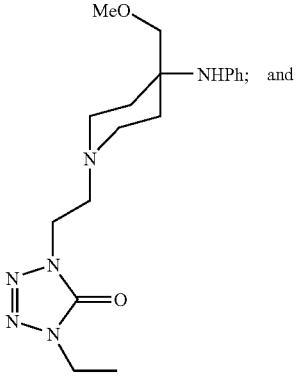

(g) acylating the alkoxymethyl-N-substituted tetrazole-piperidine product to form an acylated alkoxymethyl-N-substituted tetrazole-piperidine product, alfentanil, having the structure

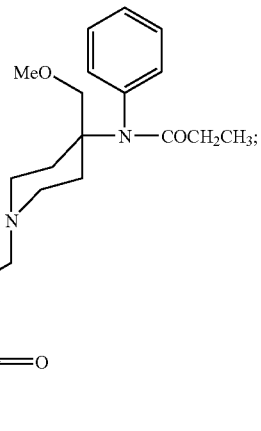

wherein n is an integer from 0 to about 10 and

R is $C_{1-6}$ alkyl.

* * * * *